US009339760B2

(12) United States Patent
Kennedy et al.

(10) Patent No.: US 9,339,760 B2
(45) Date of Patent: May 17, 2016

(54) METHODS AND APPARATUSES FOR REMOVAL OF HYDROGEN SULFIDE AND CARBON DIOXIDE FROM BIOGAS

(71) Applicants: Nicholas Kennedy, Huntington Beach, CA (US); Quan-Bao Zhao, Pullman, WA (US); Anping Jiang, Beijing (CN); Craig Frear, Pullman, WA (US); Stephen W. Dvorak, Chilton, WI (US)

(72) Inventors: Nicholas Kennedy, Huntington Beach, CA (US); Quan-Bao Zhao, Pullman, WA (US); Anping Jiang, Beijing (CN); Craig Frear, Pullman, WA (US); Stephen W. Dvorak, Chilton, WI (US)

(73) Assignees: DVO, Inc., Chilton, WI (US); Washington State University, Pullman, WA (US)

( * ) Notice: Subject to any disclaimer, the term of this patent is extended or adjusted under 35 U.S.C. 154(b) by 214 days.

(21) Appl. No.: 13/834,494

(22) Filed: Mar. 15, 2013

(65) Prior Publication Data

US 2013/0309759 A1 Nov. 21, 2013

Related U.S. Application Data

(63) Continuation-in-part of application No. 13/157,907, filed on Jun. 10, 2011, now Pat. No. 8,613,894.

(60) Provisional application No. 61/354,156, filed on Jun. 11, 2010.

(51) Int. Cl.
*C01C 1/24* (2006.01)
*B01D 53/62* (2006.01)
(Continued)

(52) U.S. Cl.
CPC .............. *B01D 53/62* (2013.01); *C02F 3/2893* (2013.01); *C02F 3/30* (2013.01); *C05F 17/0018* (2013.01); *C05F 17/0027* (2013.01); *C05F 17/0054* (2013.01); *C12M 21/04* (2013.01);
(Continued)

(58) Field of Classification Search
CPC . B01D 53/62; C05F 17/0054; C05F 17/0018; C05F 17/0027; C02F 3/30; C02F 3/2893; C02F 2101/101; Y02E 50/343
USPC .......................... 423/545; 435/266, 296, 300
See application file for complete search history.

(56) References Cited

U.S. PATENT DOCUMENTS 2,886,405 A 5/1959 Benson et al.
4,496,371 A 1/1985 Urban et al.
(Continued)

FOREIGN PATENT DOCUMENTS

CA 1161577 1/1984
DE 4415017 11/1995
(Continued)

OTHER PUBLICATIONS

International Search Report and Written Opinion for PCT/US14/22545 dated Mar. 10, 2014, 7 pages.
(Continued)

*Primary Examiner* — Colleen Dunn
*Assistant Examiner* — Haytham Soliman
(74) *Attorney, Agent, or Firm* — Whyte Hirschboeck Dudek S.C.

(57) ABSTRACT

Methods, systems and apparatuses herein provide a unique and novel process to remove $H_2S$ from biogas. Methods, systems and apparatuses herein provide a unique and novel process to remove $H_2S$ from biogas with ease of operation and reduced operating and capital costs. Methods, systems and apparatuses herein provide a unique and novel process to remove $H_2S$ over $CO_2$ from biogas.

11 Claims, 22 Drawing Sheets

(51) Int. Cl.
  *C05F 17/00* (2006.01)
  *C02F 3/28* (2006.01)
  *C02F 3/30* (2006.01)
  *C12M 1/107* (2006.01)
  *C12M 1/00* (2006.01)
  *C02F 101/10* (2006.01)

(52) U.S. Cl.
  CPC .............. *C12M 47/10* (2013.01); *C12M 47/18* (2013.01); *C02F 2101/101* (2013.01); *Y02E 50/343* (2013.01); *Y02P 20/145* (2015.11); *Y02W 30/43* (2015.05); *Y02W 30/47* (2015.05)

(56) References Cited

U.S. PATENT DOCUMENTS

| | | | |
|---|---|---|---|
| 4,503,154 | A | 3/1985 | Paton |
| 5,015,384 | A | 5/1991 | Burke |
| 5,316,682 | A * | 5/1994 | Keyser et al. ............... 210/649 |
| 5,670,047 | A | 9/1997 | Burke |
| 6,368,849 | B1 | 4/2002 | Norddahl |
| 6,451,589 | B1 | 9/2002 | Dvorak |
| 6,500,340 | B1 | 12/2002 | Burke |
| 6,613,562 | B2 | 9/2003 | Dvorak |
| 6,866,779 | B1 | 3/2005 | Burke |
| 6,946,076 | B2 | 9/2005 | Mills |
| 7,014,768 | B2 | 3/2006 | Li et al. |
| 7,078,229 | B2 | 7/2006 | Dvorak |
| 7,153,427 | B2 | 12/2006 | Burke |
| 7,166,220 | B2 | 1/2007 | Tanaka et al. |
| 7,179,642 | B2 | 2/2007 | Dvorak |
| 7,371,328 | B1 | 5/2008 | Hokanson et al. |
| 7,410,589 | B2 | 8/2008 | Lakshman |
| 7,550,610 | B1 * | 6/2009 | Chang et al. .............. 549/533 |
| 7,604,740 | B2 | 10/2009 | Baur |
| 7,785,467 | B2 | 8/2010 | Logan et al. |
| 7,806,957 | B1 | 10/2010 | Burke |
| 7,811,455 | B2 | 10/2010 | Burke |
| 7,909,995 | B2 | 3/2011 | Jiang et al. |
| 8,202,721 | B2 | 6/2012 | Dvorak |
| 8,613,894 | B2 | 12/2013 | Zhao et al. |
| 2002/0096471 | A1 | 7/2002 | Miller, III |
| 2003/0038078 | A1 | 2/2003 | Stamper et al. |
| 2004/0164019 | A1 | 8/2004 | Fassbender |
| 2004/0164021 | A1 | 8/2004 | Li et al. |
| 2007/0101783 | A1 | 5/2007 | Gross et al. |
| 2007/0102352 | A1 | 5/2007 | Burke |
| 2008/0053909 | A1 | 3/2008 | Fassbender |
| 2008/0156726 | A1 | 7/2008 | Fassbender |
| 2009/0062581 | A1 | 3/2009 | Appel et al. |
| 2009/0156875 | A1 | 6/2009 | Tomioka et al. |
| 2009/0206028 | A1 * | 8/2009 | Jiang et al. ............... 210/603 |
| 2010/0024647 | A1 | 2/2010 | Gunther |
| 2010/0032370 | A1 | 2/2010 | Allen et al. |
| 2012/0048801 | A1 | 3/2012 | Hong et al. |
| 2012/0118035 | A1 | 5/2012 | Zhao et al. |
| 2012/0156744 | A1 | 6/2012 | MacDonald et al. |

FOREIGN PATENT DOCUMENTS

| | | |
|---|---|---|
| JP | 61133200 | 6/1986 |
| JP | 2002079299 | 3/2002 |
| KR | 100414917 | 12/2003 |
| WO | WO9119558 | 12/1991 |
| WO | 2004011393 | 2/2004 |
| WO | WO2004054688 | 7/2004 |

OTHER PUBLICATIONS

Equivalent-Abstracts: Inorganic Chemistry.
Frear, C. et al., "An Integrated Pathogen Control, Ammonia and Phosphorus Recovery System for MAnure and/or Organic Wastes," Washington State University, Separtment of Biological Systems Engineering, May 11-12, 2-011.
Jaing, A. et al., "Integrated ammonia recover technology in conjunction with dairy anaerobic digestion," CFF Final Report-AD Component, Jun. 4, 2010.
Frear, C. et al., "An integrated nutrient recover, Class-A fiber production process, and h2S scrubbing system that works in series with dairy manure anaerobic digesters-farm-scale demonstration on tow Washington State sairies with digesters.", NRCS CIG WSU Nutrient REceover.
Zhao, Q et al., "Phosporus recovery technology in conjunction with dairy anaerobic digestion.", CFF Final Report-AD Component.
International Search Report and Written Opinion for PCT App. No. PCT/US2011/040061 mailed on Feb. 29, 2012.
International Preliminary Report on Patentability mailed on Dec. 14, 2012 for PCT App No. PCT/US2011/040061.
Examination Report for New Zealand PAL App. No. 604050 mailed on Jul. 29, 2013.

* cited by examiner

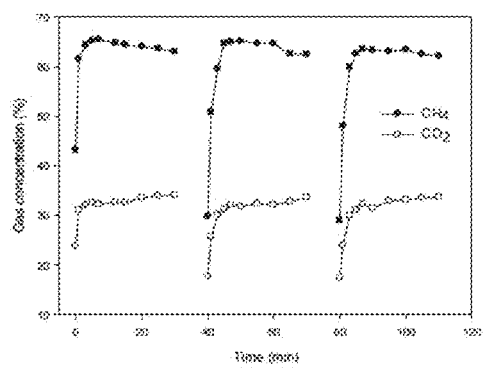 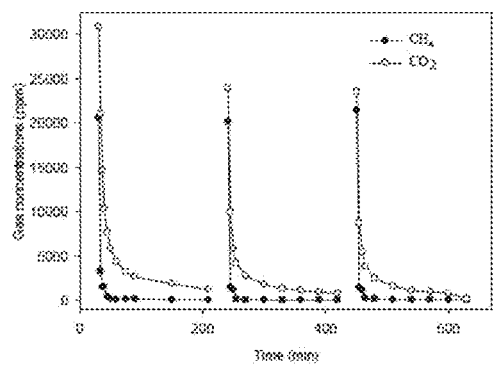
FIG. 21A                            FIG. 21B

METHODS AND APPARATUSES FOR REMOVAL OF HYDROGEN SULFIDE AND CARBON DIOXIDE FROM BIOGAS

CROSS-REFERENCE TO RELATED APPLICATIONS

This application is a continuation-in-part application of U.S. patent application Ser. No. 13/157,907 filed Jun. 10, 2011, which claims priority to U.S. Provisional Patent Application Ser. No. 61/354,156 filed Jun. 11, 2010. Each of the above-referenced applications are herein incorporated by reference in their entirety.

REFERENCE TO GOVERNMENT GRANT

This invention was made with United States government support awarded by the following agency: USDA. The United States has certain rights in this invention.

FIELD

Methods, systems and apparatuses herein provide a unique and novel process to remove $H_2S$ from biogas. In another embodiment, methods, systems, and apparatuses herein provide a process to remove $H_2S$ and $CO_2$ from a biogas. Methods, systems and apparatuses disclosed herein provide an integrated approach to waste management.

BACKGROUND

Livestock confinement facilities generate large amounts of animal waste that can create serious environmental and human health concerns. For example, animal waste constituents such as organic matter, nitrogen, phosphorus, pathogens and metals can degrade water quality, air quality, and adversely impact human health. Organic matter, for example, contains a high amount of biodegradable organics and when discharged to surface waters will compete for, and deplete the limited amount of dissolved oxygen available, causing fish kills and other undesirable impacts. Similarly nutrient loading from nitrogen and phosphorus can lead to eutrophication of surface waters.

The annual accumulation of organic waste in the world is immense. There are approximately 450,000 Animal Feeding Operations ("AFOs") in the United States. Common types of AFOs include dairies, cattle feedlots, and poultry farms. A single dairy cow produces approximately 120 pounds of wet manure per day. The waste produced per day by one dairy cow is equal to that of 20-40 people. If properly stored and used, manure from animal feeding operations can be a valuable resource.

Anaerobic digester technology is a manure management technology capable of alleviating environmental concerns through waste stabilization, odor reduction, pathogen control and greenhouse gas entrapment and mitigation, while producing a renewable source of heat and power (US-EPA, 2005). Adoption of anaerobic digesters on US dairies is growing but still slow with numbers insufficient to meet the agreement between the US and its dairy industry to reduce climate impacts from dairies by 25% by 2020 (USDA, 2010).

Anaerobic digesters utilizes microorganisms to breakdown the organic carbon in manure in the absence of oxygen producing a biogas mainly composed of methane ($CH_4$), and contaminants including carbon dioxide ($CO_2$) and hydrogen sulfide ($H_2S$). Biogas derived from the anaerobic digestion (AD) of dairy manure consists of methane ($CH_4$) (55-65%) and contaminants including carbon dioxide ($CO_2$) (30-45%), low concentrations of hydrogen sulfide ($H_2S$) (300-4,500 ppm) (Liebrand and Ling 2009).

These contaminants, without pretreatment, limit the use of biogas to combined heat and power (CHP) on-site, whereas many economic assessments have suggested that a higher value use is possible by purifying $CH_4$ to meet natural gas regulations or purifying and compressing it for use as a vehicle fuel.

$H_2S$, which is produced by the breakdown of proteins and other sulfur containing compounds during hydrolysis, is detrimental to an internal combustion engine as well as to the environment and human health. Even at low concentrations, $H_2S$ has an unpleasant odor and can be life threatening (Speece 1996). Consequently, the recommended industrial exposure limits are from 8 to 10 ppm for 8 hours a day per week (Horikawa, Rossi et al. 2004). Furthermore, this contaminant is highly non-desirable in energy-recovery processes because it converts to unhealthy and environmentally hazardous sulfur dioxide ($SO_2$) and sulfuric acid ($H_2SO_4$) (Abatzoglou and Boivin 2009). $H_2SO_4$ is neutralized by the alkalinity in the engine oil and requires frequent oil replacement or running the engines rich in fuel to decrease the contact time between the raw biogas and the engine to limit corrosion from the $H_2SO_4$ (Fulton 1991). $H_2S$ must be reduced to a level less than 4 ppm before direct injection into pipelines (Wise 1981) and completely removed from biogas if it is going to be compressed and used as a vehicle fuel.

$CO_2$ is not detrimental to equipment or human health like other impurities, but because of its comparatively high presence in biogas, it does decrease the energy potential of biogas, due to its inert nature. Due to the presence of $CO_2$ and the lower $CH_4$ content in biogas, the energy potential of biogas is around 612 BTU/scf, whereas natural gas has an energy potential of 1031 BTU/scf (Bothi 2007).

Therefore, methods and apparatuses that can remove $H_2S$ and $CO_2$ from biogas are needed and would have a tremendous impact in the industry.

BRIEF SUMMARY

Methods, systems and apparatuses herein provide a unique and novel process to remove $H_2S$ from biogas. Methods, systems and apparatuses herein provide a unique and novel process to remove $H_2S$ from biogas with ease of operation and reduced operating and capital costs.

Methods, systems and apparatuses herein provide a unique and novel process to remove $H_2S$ over $CO_2$ from biogas. Methods, systems and apparatuses herein provide a unique and novel process to selectively remove $H_2S$ over $CO_2$ from biogas.

Methods, systems and apparatuses herein provide a unique and novel process to first remove $H_2S$ over $CO_2$ from biogas and then in a second step to remove remaining $CO_2$ from the biogas. In one embodiment, an alkaline effluent is used to remove the $H_2S$ from the biogas. In another embodiment, an alkaline effluent is used to remove $CO_2$ from biogas.

In yet another embodiment, a single effluent is used to remove $H_2S$ and $CO_2$ in biogas. The single effluent may be regenerated after removal of $H_2S$ in biogas. Regeneration comprises returning the effluent to an alkaline pH. In another embodiment, a first alkaline effluent is used to remove $H_2S$ from biogas and a second, independent alkaline effluent is sued to remove $CO_2$ in biogas.

Methods, systems and apparatuses disclosed herein provide for production of an alkaline liquid effluent. In one embodiment, the alkaline effluent is from an anaerobic digester. In another embodiment, the alkaline effluent is generated by anaerobic digestions of waste material followed by aeration of the effluent to release super-saturated gases and allow for the recovery of nutrients from the effluent.

Methods, systems and apparatuses disclosed herein provide for the use of alkaline liquid effluent for selectively removing $H_2S$ over $CO_2$ in a biogas.

Methods, systems and apparatuses disclosed herein provide for the regeneration of an alkaline liquid effluent so that additional contaminants, including but not limited to remaining $H_2S$ and $CO_2$, can be removed from the biogas.

Methods, systems and apparatuses disclosed herein can be used to increase the quantity of biogas capture from the anaerobic digester. Methods, systems and apparatuses disclosed herein can be used to increase the purity of biogas from the anaerobic digester.

In one embodiment, the disclosure relates to a method for removing contaminants in a biogas comprising: (a) heating and aerating anaerobic digester effluent in an aeration reactor to produce an alkaline effluent; (b) contacting the alkaline effluent from step (a) with an input biogas in a reactor to produce a treated biogas and a resulting effluent with a lower pH as compared to the pH of the alkaline effluent; and (c) recovering the treated biogas from step (b), wherein the treated biogas has less $H_2S$ as compared to the input biogas.

In another embodiment, the disclosure relates to a method for removing contaminants in a biogas comprising: (a) heating and aerating an anaerobic digester effluent in an aeration reactor to produce an alkaline effluent; (b) contacting the alkaline effluent from step (a) with an input biogas in a reactor to produce a treated biogas and a resulting effluent with a lower pH as compared to the pH of the alkaline effluent; (c) recovering the treated biogas from step (b), wherein the treated biogas has less $H_2S$ as compared to the input biogas; (d) aerating the resulting effluent of step (b) to produce a regenerated effluent with an alkaline pH; and (e) contacting the regenerated alkaline effluent of step (d) with the recovered biogas of step (c) to remove $CO_2$ in the biogas.

In one embodiment, the disclosure relates to a method comprising treating biogas produced from an anaerobic digester with an alkaline effluent to remove $H_2S$ from the biogas. In one embodiment, the alkaline effluent is produced by anaerobic digestion. In an embodiment, the alkaline effluent is produced as a by-product of the anaerobic digestion of manure and subsequent removal of $NH_3$ (a nutrient recovery process). In yet another embodiment, the $NH_3$ is removed by aerating the effluent.

In an embodiment, a method removing contaminants from a biogas is provided comprising: (a) digesting waste material in an anaerobic digester to produce a biogas; (b) aerating anaerobic digester effluent to produce an alkaline effluent; (c) treating the biogas from step (a) with the alkaline liquid effluent from step (b) to remove $H_2S$ and a produce biogas composed mainly of $CH_4$ and $CO_2$. In yet another embodiment, the method comprises prior to step (b), separating digested material in step (a) from effluent. In yet another embodiment, the method comprises prior to step (b), separating digested fibrous material in step (a) from effluent.

In another embodiment, separating digested material in step (a) from effluent can be achieved through the use of mechanical methods including but not limited to screens, filters, and column separation.

In another embodiment, a method for removing contaminants from a biogas is provided comprising: (a) digesting waste material in an anaerobic digester to produce an effluent and a biogas; (b) aerating anaerobic digester effluent to produce an alkaline effluent; (c) treating the biogas from step (a) with the alkaline liquid effluent from step (b) to selectively remove $H_2S$ over $CO_2$ to produce a biogas composed mainly of $CH_4$ and $CO_2$ and a resulting effluent with a lower pH than the pH of the alkaline effluent; (d) regenerating the resulting effluent from step (d); and (e) treating the biogas with the regenerated effluent from step (d) to remove $CO_2$ from the biogas. In yet another embodiment, steps (d) and (e) can be repeated any number of times, including but not limited to 2, 3, 4, 5, 6, 7, 8, 9, 10, 11, 12, 13, 14, 15, and greater than 15 times. In one embodiment, regenerating the resulting effluent from step (d) comprises aerating the resulting effluent.

In another embodiment, a method for removing contaminants from a biogas is provided comprising: (a) digesting waste material in an anaerobic digester to produce an effluent and a biogas; (b) aerating anaerobic digester effluent to release supersaturated gases and produce an alkaline effluent; (c) treating the biogas from step (a) with the alkaline liquid effluent from step (b) to selectively remove $H_2S$ over $CO_2$ and produce a biogas composed mainly of $CH_4$ and $CO_2$; (d) regenerating an effluent fraction produced along the manure management cycle to produce a regenerated alkaline effluent; and (e) treating the biogas with the regenerated effluent from step (d) to remove $CO_2$ from the biogas. In one embodiment, regenerating the effluent fraction is achieved by aerating the effluent fraction.

In another embodiment, the regenerated alkaline effluent is produced from the aeration of any number of various solid-containing digester effluent fractions produced along the manure management and screening system housed on the farm. In one embodiment, the effluent fraction to be regenerated is a fibrous containing effluent fraction. In another embodiment, the effluent fraction to be regenerated is a fine solids containing effluent.

In another embodiment, a method removing contaminants from a biogas is provided comprising: (a) digesting waste material in an anaerobic digester to produce a biogas; (b) aerating anaerobic digester effluent to produce an alkaline effluent; (c) treating the biogas from step (a) with the alkaline liquid effluent from step (b) to selectively remove $H_2S$ over $CO_2$ to produce a biogas composed mainly of $CH_4$ and $CO_2$, (d) regenerating the effluent from step (d) by aerating the alkaline effluent and producing an effluent with a pH lower than the pH of the effluent prior to aeration; and (e) treating the biogas with the effluent from step (d) to remove $CO_2$ from the biogas. In yet another embodiment, steps (d) and (e) can be repeated any number of times, including but not limited to 2, 3, 4, 5, 6, 7, 8, 9, 10, 11, 12, 13, 14, 15, and greater than 15 times.

In yet another embodiment, the disclosure relates to a system comprising: an aeration reactor for heating and aerating anaerobic digester effluent, wherein heating and aerating the effluent produces an alkaline effluent; a reactor for contacting the alkaline effluent with an input biogas to produce a treated biogas and a resulting effluent with a lower pH as compared to the pH of the alkaline effluent; and a vessel for collecting treated biogas, wherein the treated biogas has less $H_2S$ than the input biogas.

In an embodiment, an apparatus for treating biogas is provided.

In one embodiment, the apparatus comprises a bubble column. In one embodiment, the apparatus comprises a vessel with a gas headspace above the liquid level and below the vessel ceiling. In an embodiment, the vessel would be airtight.

In one embodiment, the disclosure relates to method comprising anaerobically digesting dairy manure to produce an effluent, stripping ammonia from the anaerobically digested effluent to produce an alkaline (e.g., pH>9.7) effluent. In another embodiment, the anaerobically digested effluent is used to purify biogas of $H_2S$ (and some $CO_2$). In another embodiment, the method comprises regenerating the effluent by aerating the effluent. The regenerated effluent can be used to clean the biogas of $CO_2$.

An advantage of the methods, systems and apparatuses disclosed herein is that the alkaline effluent used to remove the $H_2S$ is in continual supply. The alkaline effluent can be recycled and used in multiple applications.

An advantage of the methods, systems and apparatuses disclosed herein is that $H_2S$ can be selectively removed in a $CO_2$-rich biogas.

An advantage of the methods, systems and apparatuses disclosed herein is that the alkaline liquid effluent used to remove the $H_2S$ can be used as a fertilizer.

An advantage of the methods, systems and apparatuses disclosed herein is that effluent, post purification, has nutrients including but not limited to carbon and sulfur, for planting applications compared with just regular effluent coming out of the digester.

An advantage of the methods, systems and apparatuses disclosed herein is that there is no need to purchase chemical absorbents to remove $H_2S$ from the biogas or to alter the pH of the liquid effluent.

An advantage of the methods, systems and apparatuses disclosed herein is that there is no need for disposal of chemical absorbents used to remove $H_2S$ from the biogas.

An advantage of the methods, systems and apparatuses disclosed herein is that the alkaline effluent can be regenerated and used to remove remaining $CO_2$ from the biogas.

An advantage of the methods, systems and apparatuses disclosed herein is that the alkaline effluent can be regenerated without the use of expensive chemicals.

An advantage of the methods, systems and apparatuses disclosed herein is that the alkaline effluent can be regenerated by aeration.

An advantage of the methods, systems and apparatuses disclosed herein is that they provide for decreased capital and maintenance costs.

An advantage of the methods, systems and apparatuses disclosed herein is that they provide a simple but effective process to reduce the concentration of $H_2S$ in biogas prior to combustion in an engine, thereby decreasing maintenance costs and increasing the lifespan of the engine.

An advantage of the methods, systems and apparatuses disclosed herein is that they provide a simple but effective process to reduce the concentration of $H_2S$ in biogas and can be integrated as a downstream biogas upgrading process at agricultural digesters utilizing nutrient recovery methods and techniques.

BRIEF DESCRIPTION OF THE DRAWINGS

FIG. 21A is a graph depicting the component gas concentrations leaving the top of the apparatus after gas purification processing.

FIG. 21B is a graph depicting the component gas concentrations leaving the top of the apparatus after effluent regeneration processing.

Figure 1:
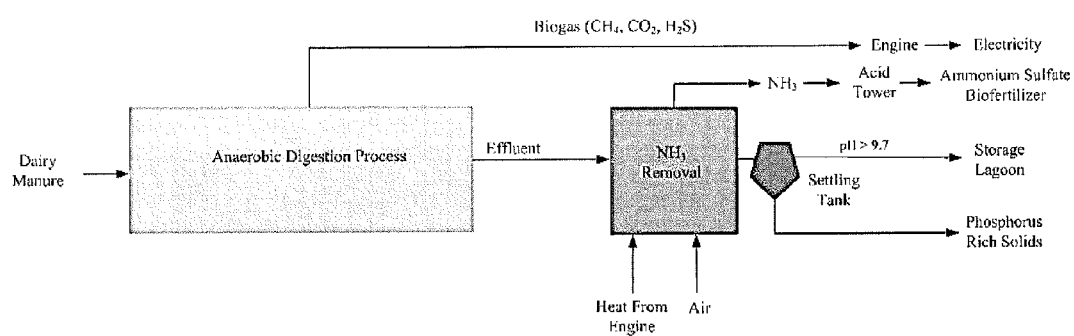
FIG. 1 is a schematic depicting a system comprising an anaerobic digester, a nutrient recovery process and a biogas purification process. Waste material is anaerobically digested, which produces a biogas and a liquid product known as effluent. The nutrient recovery system, utilized to recover nitrogen and phosphorous, produces an alkaline effluent. The alkaline effluent is used to purify biogas by removing $H_2S$ and $CO_2$. After biogas purification, the effluent, with a lower pH, can be used as fertilizer and/or stored in a lagoon.

Before one embodiment of the invention is explained in detail, it is to be understood that the invention is not limited in its application to the details of construction and the arrangements of the components set forth in the following description or illustrated in the drawings. The methods and apparatuses are capable of other embodiments and of being practiced or being carried out in various ways. Also, it is understood that the phraseology and terminology used herein is for the purpose of description and should not be regarded as limiting. The use of "including" and "comprising" and variations thereof herein is meant to encompass the items listed thereafter and equivalents thereof as well as additional items.

DETAILED DESCRIPTION

Definitions

The numerical ranges in this disclosure are approximate, and thus may include values outside of the range unless otherwise indicated. Numerical ranges include all values from and including the lower and the upper values, in increments of one unit, provided that there is a separation of at least two units between any lower value and any higher value. As an example, if a compositional, physical or other property, such as, for example, molecular weight, viscosity, melt index, etc., is from 100 to 1,000, it is intended that all individual values, such as 100, 101, 102, etc., and sub ranges, such as 100 to 144, 155 to 170, 197 to 200, etc., are expressly enumerated. For ranges containing values which are less than one or containing fractional numbers greater than one (e.g., 1.1, 1.5, etc.), one unit is considered to be 0.0001, 0.001, 0.01 or 0.1, as appropriate. For ranges containing single digit numbers less than ten (e.g., 1 to 5), one unit is typically considered to be 0.1. These are only examples of what is specifically intended, and all possible combinations of numerical values between the lowest value and the highest value enumerated, are to be considered to be expressly stated in this disclosure. Numerical ranges are provided within this disclosure for, among other things, relative amounts of components in a mixture, and various temperature and other parameter ranges recited in the methods.

As used herein, the singular forms "a," "an," and "the" refer to one or more than one, unless the context clearly dictates otherwise.

As used herein, the term "anaerobic digester effluent" refers to effluent produced at any stage during a manure management lifecycle. Anaerobic digester effluent includes effluent directly removed from the anaerobic digester, effluent removed from the digester and separated from large solids, effluent removed from the digester and separated from fine solids, effluent removed from the digester and separated from large and fine solids; effluent removed from the digester and aerated; effluent removed from the digester and heated; effluent removed from the digester and heated and aerated; effluent removed from the digester heated and aerated and separated from solids; effluent removed from the digester heated, aerated and used to remove $H_2S$ from a biogas, effluent removed from the digester heated, aerated, separated from solids; used to remove $H_2S$ from biogas; effluent removed from the digester heated, aerated, used to remove $H_2S$ from a biogas and regenerated to an alkaline pH; effluent removed from the digester heated, aerated, separated from solids; used to remove $H_2S$ from biogas, and regenerated to an alkaline pH; effluent removed from the digester heated, aerated, used to remove $H_2S$ from a biogas, regenerated to an alkaline pH, and used to remove $CO_2$ from a biogas; and effluent removed from the digester heated, aerated, separated from solids; used to remove $H_2S$ from biogas, regenerated to an alkaline pH and used to remove $CO_2$ from biogas. Anaerobic digester effluent and effluent may be used interchangeably unless stated otherwise.

As used herein, the terms "bioreactor," "reactor," or "fermentation bioreactor," include a fermentation device consisting of one or more vessels and/or towers or piping arrangement, which includes the Continuous Stirred Tank Reactor (CSTR), Immobilized Cell Reactor (ICR), Trickle Bed Reactor (TBR), Bubble Column, Gas lift Fermenter, Static Mixer, or other device suitable for gas-liquid contact.

As used herein, the term "includes" means "comprises." For example, a device that includes or comprises "A" and "B" contains "A" and "B" but may optionally contain "C" or other components other than "A" and "B." A device that includes or comprises "A" or "B" may contain "A" or "B" or "A" and "B," and optionally one or more other components such as "C."

As used herein, the term "manure" is meant to refer herein to animal wastes including animal dejections, feed remains and hair.

As used herein, the term "quicklime" is calcium oxide (CaO). Quicklime is a white, caustic and alkaline crystalline solid at room temperature. As a commercial product, lime often also contains magnesium oxide, silicon oxide and smaller amounts of aluminum oxide and iron oxide.

As used herein, the term "removing or reducing $CO_2$" refers to eliminating an amount or percentage of $CO_2$ in biogas. The percentage eliminated can be as small as 0.5% or greater than 200%.

As used herein, the term "removing or reducing $H_2S$" refers to eliminating an amount or percentage of $H_2S$ in biogas. The percentage eliminated can be as small as 0.5% or greater than 200%.

As used herein, the term "treated biogas" refers to biogas that has been in direct or indirect contact with an alkaline effluent.

Methods, systems and apparatuses disclosed herein can be used to remove $H_2S$ from biogas. Methods, systems and apparatuses disclosed herein can be used to remove $H_2S$ and $CO_2$ from biogas. In one embodiment, methods, systems and apparatuses disclosed herein are aimed at producing a biogas that can be used as fuel and for electricity.

In one embodiment, the methods, systems and apparatuses herein provide for integration, wherein the by-products from one unit of operation are used for treatment in a subsequent unit of operation. The major chemical and energy inputs to the system are (a) biogas comprising $CH_4$ and contaminants including $CO_2$ and $H_2S$; and (b) an alkaline liquid effluent. In exchange, multiple saleable and useable products are developed—a lean biogas with reduced $H_2S$ as compared to the starting biogas; and a liquid effluent that can be applied as a fertilizer.

In one embodiment, a system is designed to work in conjunction with an anaerobic digester and a nutrient recovery system for the treatment and recovery of saleable biogas. Methods, systems, and apparatuses disclosed herein can work with any type of anaerobic digester including but not limited agricultural digesters, farm digesters, municipal digesters, industrial digesters, and commercial digesters Methods, systems, and apparatuses disclosed herein can work on any type of farm including a flush dairy farm and a scrape dairy farm.

In one embodiment, methods, systems and apparatuses disclosed herein comprise aeration technology to aerate the effluent from digested waste material to remove supersaturated $CO_2$, and to increase the pH of the effluent to a value ranging from 7 to 12. The increase in pH will aid in the settling of the solids. In another embodiment, methods, systems and apparatuses disclosed herein comprise the addition of an agent with a high pH value including but not limited to a caustic or quicklime to increase the pH to a value ranging from 7 to 12.0.

In one embodiment, systems disclosed herein have multiple levels of treatment possibilities. The system can be tailored to a particular anaerobic digester in any setting, meeting its unique needs, while keeping costs controlled, and within a budget.

Methods, systems and apparatuses disclosed herein avoid the input and use of expensive chemical additives.

Methods, systems and apparatuses disclosed herein can be used to selectively remove $H_2S$ over $CO_2$.

Methods, systems and apparatuses disclosed herein can be used to selectively remove $H_2S$ over $CO_2$ in a first step, and in a second step, remove remaining $CO_2$ in the biogas.

Methods, systems and apparatuses disclosed herein can use an alkaline digester effluent to selectively remove $H_2S$ over $CO_2$, regenerate the effluent to an alkaline pH, and remove the remaining $CO_2$ in the biogas using the regenerated alkaline effluent.

Methods, systems and apparatuses disclosed herein can be used to reduce $H_2S$ in the biogas including but not limited to a reduction of 5-10%, 10-20%, 20-30%, 30-40%, 40-50%, 50-60%, 60-70%, 70-80%, 80-90%, 90-95%, and 95-99% as compared to the amount of $H_2S$ in the starting or untreated biogas.

Methods, systems and apparatuses disclosed herein can be used to reduce $CO_2$ in the biogas including but not limited to a reduction of 5-10%, 10-20%, 20-30%, 30-40%, 40-50%, 50-60%, 60-70%, 70-80%, 80-90%, 90-95%, and 95-99% as compared to the amount of $CO_2$ in the starting or untreated biogas.

System for Removal of Contaminants in Biogas

In one embodiment, a system for removal of contaminants in biogas 10 is illustrated in FIG. 1. The system 10 includes a nutrient recovery system (3), a settling tank (5), and a vessel for the removal of $H_2S$ (7) in the biogas. The system 10 can be used to process waste material and remove contaminants, including $H_2S$, from biogas, thereby producing a biogas that can be used for electricity and as a fuel source.

The nutrient recovery system includes the anaerobic digestion process, solid separation for phosphorous removal, $NH_3$ removal via air stripping and acid absorption with an appropriate acid, such as sulfuric acid ($H_2SO_4$). The heat required in the $NH_3$ process can be recovered from the CHP engine.

As can be seen from the schematic in FIG. 1, at the end of the nutrient recovery process, the effluent is at a pH of around 9.7, which should be reduced before storage in a lagoon or applied as a fertilizer. Since the pH of the effluent is high it is a suitable candidate to be used as an absorbent for biogas purification. The alkaline effluent is a suitable candidate for the removal of contaminants including but not limited to $H_2S$ and $CO_2$, from raw biogas.

Nutrient Recovery System

Figure 2:
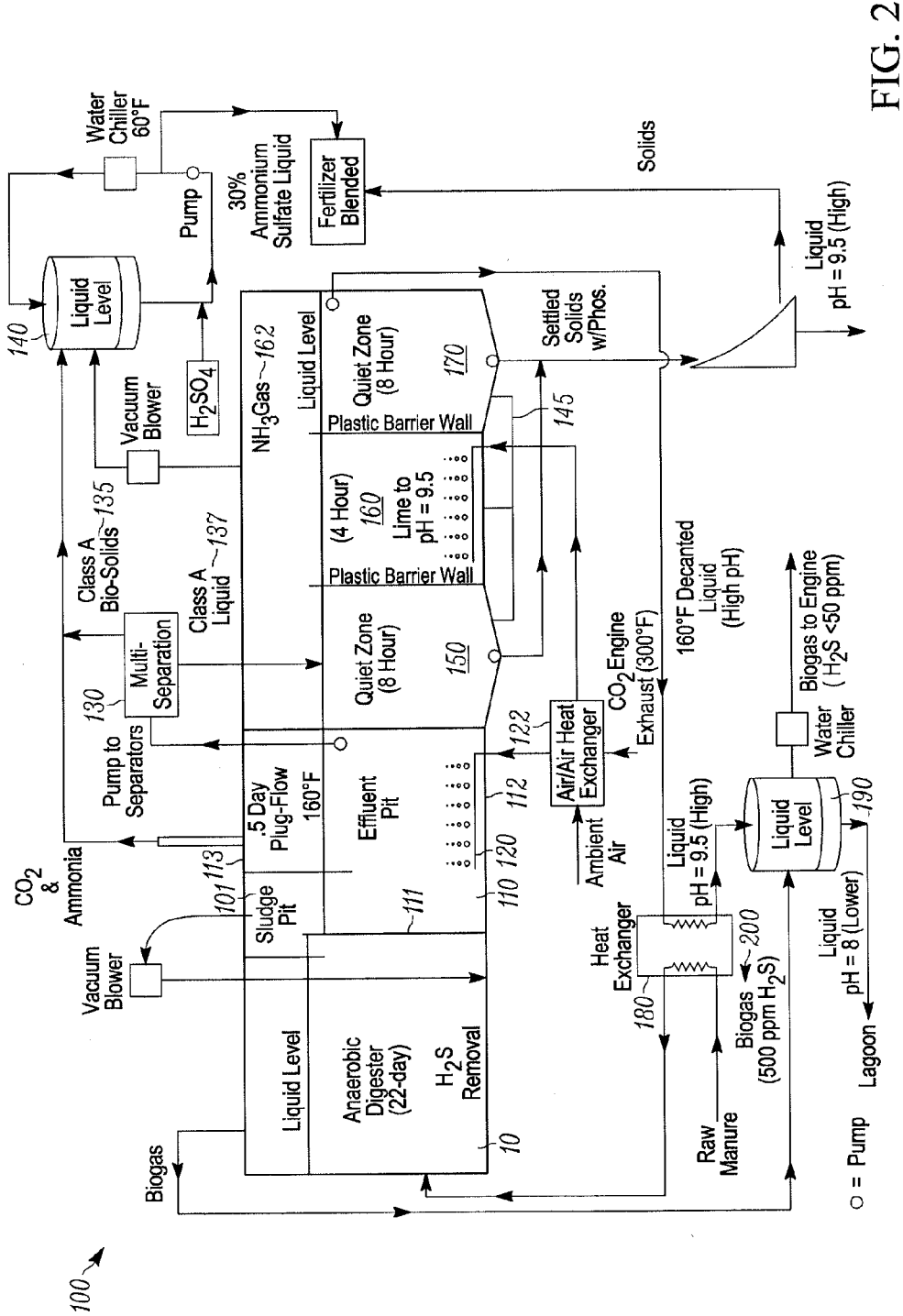
FIG. 2 is a schematic of one embodiment of a nutrient recovery system showing a three-chambered air-tight vessel.

In one embodiment, a nutrient recovery system 100 is illustrated in FIG. 2. The nutrient recovery system comprises an anaerobic digester (10) for digesting of waste material. Waste material may be collected using any suitable means in the art. One example of a nutrient recovery system is disclosed in U.S. Patent Application Publication No. 2012/0118305, which is incorporated by reference herein in its entirety.

Waste material includes but is not limited to wood, grass, agricultural residue, manure, recycled waste paper, and agricultural waste materials. Examples of sources of waste materials include, but are not limited to, livestock production facilities, such as cattle, swine, goat, sheep, dairy cow, horse and the like, chicken ranches, turkey farms, duck farms, geese farms, human waste, and the like. Waste material may also include many forms of agricultural products processing facilities that may include non-food related agricultural products. Waste material may also include some forms of commingled wastes where a portion of the waste may also include food scraps. Waste material also may include commingled fibers with spoiled foods.

In another embodiment, the waste material also may include hay, straw, and other material commonly used in animal stalls or other agriculture environment. In yet another embodiment, the waste material also may contain urine plus water used in cleaning the stalls. In still yet another embodiment, the waste material may also contain additional material, such as twine, rope, and other material that may or may not be biodegradable. In yet another embodiment, the waste material is from a dairy farm.

In another embodiment, the waste material also may include fibers from non-food agricultural products such as bamboo, oil palm, coir, etc.

Any type of anaerobic digester may be used. A conventional anaerobic digester system generally includes the following components: manure transfer and mixing pit, a digester made of steel, fiberglass, concrete, earth or other suitable material (including heating and mixing equipment if needed), biogas handling and transmission, and gas end use (combustion) equipment such as electric generation equipment.

Conventional anaerobic digesters can also require significant operational oversight depending on operational mode and temperature. Conventional anaerobic digester systems also require proper design and sizing to maintain critical bacterial populations responsible for waste treatment and stabilization for sustained long-term predictable performance. Sizing requirements are based on hydraulic retention time (HRT), and loading rate, where the operating temperature affects these sizing parameters. These factors (size, materials, operational requirements) affect digester costs, which may be fairly capital intensive, and in some economies and farm scales, may not be affordable or may be inoperable if experienced technicians are not available.

In one embodiment, anaerobic digesters having any type of process configuration can be used including but not limited to batch, continuous, mesophilic temperature, thermophilic temperature, high solids, low solids, single-stage complexity and multistage complexity.

In another embodiment, a batch system of anaerobic digestion can be used. Biomass is added to the reactor at the start of the process in a batch and is sealed for the duration of the process. Batch reactors suffer from odor issues that can be a severe problem when they are emptied. Typically biogas production will be formed with a normal distribution pattern over time. The operator can use this fact to determine when they believe the process of digestion of the organic matter has completed.

In yet another embodiment, a continuous system of anaerobic digestion can be used. In continuous digestion processes, organic matter is typically added to the reactor in stages. The end products are constantly or periodically removed, resulting in constant production of biogas. Examples of this form of anaerobic digestion include, continuous stirred-tank reactors (CSTRs), Upflow anaerobic sludge blanket (UASB), Expanded granular sludge bed (EGSB) and Internal circulation reactors (IC).

In still another embodiment, mesophilic or thermophilic operational temperature levels for anaerobic digesters can be used. Mesophilic temperature levels take place optimally around 37°-41° C. or at ambient temperatures between 20°-45° C.; under these temperatures, mesophiles are the primary microorganism present. Thermophilic temperature levels take place optimally around 50°-52° C. and at elevated temperatures up to 70° C.; under these temperatures, thermophiles are the primary microorganisms present.

There are a greater number of species of mesophiles than thermophiles. Mesophiles are also more tolerant to changes in environmental conditions than thermophiles. Mesophilic systems are therefore considered to be more stable than thermophilic digestion systems.

In another embodiment, anaerobic digesters can either be designed to operate in a dry-solids, not liquefied content, with a total suspended solids (TSS) concentration greater than 20%, or a low solids concentration with a TSS concentration less than 15%. High-solids digesters process a thick slurry that requires more energy input to move and process the feedstock. The thickness of the material may also lead to associated problems with abrasion. High-solids digesters will typically have a lower land requirement due to the lower volumes associated with the moisture.

Low-solids (high solids, liquefied) digesters can transport material through the system using standard pumps that require significantly lower energy input. Low-solids digesters require a larger amount of land than high-solids due to the increased volumes associated with the increased liquid:feedstock ratio of the digesters. There are benefits associated with operation in a liquid environment as it enables more thorough circulation of materials and contact between the bacteria and food. This enables the bacteria to more readily access the substances they are feeding off and increases the speed of gas yields.

In still another embodiment, digestion systems can be configured with different levels of complexity: one-stage or single-stage and two-stage or multistage. A single-stage digestion system is one in which all of the biological reactions occur within a single sealed reactor or holding tank. Utilizing a single-stage reactor reduces the cost of construction; however there is less control of the reactions occurring within the system. For instance, acidogenic bacteria, through the production of acids, reduce the pH of the tank, while methanogenic bacteria operate in a strictly defined pH range. Therefore, the biological reactions of the different species in a single-stage reactor can be in direct competition with each other. Another one-stage reaction system is an anaerobic lagoon. These lagoons are pond-like earthen basins used for the treatment and long-term storage of manures. In this case, the anaerobic reactions are contained within the natural anaerobic sludge contained in the pool.

In a two-stage or multi-stage digestion system, different digestion vessels are optimized to bring maximum control over the bacterial communities living within the digesters. Acidogenic bacteria produce organic acids and grow and reproduce faster than methanogenic bacteria. Methanogenic bacteria require stable pH and temperature in order to optimize their performance.

The residence time in a digester varies with the amount and type of waste material, the configuration of the digestion system and whether it is one-stage or two-stage. In the case of single-stage thermophilic digestion residence times may be in the region of 14 days, which comparatively to mesophilic digestion is relatively fast. The plug-flow nature of some of these systems will mean that the full degradation of the material may not have been realized in this timescale. In this event, digestate exiting the system will be darker in color and will typically have more odor associated with it.

In two-stage mesophilic digestion, residence time may vary between 15 and 40 days. In the case of mesophilic UASB digestion, hydraulic residence times can be (1 hour-1 day) and solid retention times can be up to 90 days. In this manner, the UASB system is able to separate solid and hydraulic retention times with the utilization of a sludge blanket.

Continuous digesters have mechanical or hydraulic devices, depending on the level of solids in the material, to mix the contents enabling the bacteria and the food to be in contact. They also allow excess material to be continuously extracted to maintain a reasonably constant volume within the digestion tanks.

In one embodiment, the waste material can be processed through an anaerobic digester available from DVO, Inc. (Chilton, Wis.). In one embodiment, the waste material can be processed through an anaerobic digester as described in any of U.S. Pat. Nos. 6,451,589; 6,613,562; 7,078,229; and 7,179,642; each of which are incorporated by reference in their entirety. Each of the patents recited above is assigned to GHD, Inc., which is now DVO, Inc., and names Mr. Steve Dvorak as the sole inventor. In yet another embodiment, the anaerobic digester can be a two-stage mixed plug flow digester system In another aspect, the disclosure may provide a method for the anaerobic digestion of high-solids waste comprising moving the solid waste in a corkscrew-like fashion through the digester. The digester is a generally U-shaped tank with overall horizontal dimensions of approximately 100 feet long and 72 feet wide. A center wall approximately 90 feet in length divides the digester into the two legs of the U-shape. Thus, each leg of the digester is approximately 100 feet long and 36 feet wide.

Modified plug flow or slurry flow can be used to move the sludge. The digester heating pipes locally heat the sludge using hot water at approximately 160° F. from the cooler of the engine, causing the heated mixed sludge to rise under convective forces. The convection develops a current in the digester that is uncharacteristic of other digesters. Sludge is heated by the digester heating pipes near the digester center wall, such that convective forces cause the heated sludge to rise near the center wall. At the same time, sludge near the relatively cooler outer wall falls under convective forces. As a result, the convective forces cause the sludge to follow a circular flow path upward along the center wall and downward along the outer wall. At the same time, the sludge flows along the first and second legs of the digester, resulting in a combined corkscrew-like flow path for the sludge.

In another embodiment (not shown), hot gas injection jets using heated gases from the output of the engine replace the hot water digester heating pipes as a heating and current-generating source. The injection of hot gases circulates the sludge through both natural and forced convection. A similar corkscrew-like flow path is developed in the digester.

To further increase upward flow of the heated sludge near the center wall, biogas may be removed from the biogas storage area in the digester, pressurized with a gas centrifugal or rotary-lobe blower, and injected into the heated sludge through nozzles positioned onto conduit. This recycled biogas injection near the floor of the digester serves to increase the rapidity of the cork-screw-like flow path for the heated sludge.

The U-shape of the digester results in a long sludge flow path and thus a long residence time of approximately twenty days. As the sludge flows through the digester, anaerobic digestion processes the sludge into activated sludge. From the digester, the activated sludge flows into the optional clarifier and into effluent pit 110. The clarifier uses gravity to separate the activated sludge into liquid and solid portions.

Effluent Pit

In one embodiment, the anaerobic digester effluent may gravity flow, or it can be pumped, into an insulated effluent pit 110. In an embodiment, the anaerobic digester effluent is discharged from the digester, while maintaining gas integrity. The discharge of the anaerobic digester effluent is designed to maximize turbulence, thin film flow, and contact with outside air. This discharge process results in degassing of supersaturated methane gas for greater gas production and environmental/climate control.

In an embodiment, the resulting methane/air mixture can be re-injected into the anaerobic digester for enhancing mixing, and increasing biogas production. In addition, the re-injected methane/air mixture can aid in reducing hydrogen sulfide content in the digester.

The temperature of the anaerobic digester effluent may be raised as it flows through the first vessel in a plug flow process to a suitable temperature including but not limited to 100° F. to 110° F., 110° F. to 120° F., 120° F. to 130° F., 130° F. to 140° F., 140° F. to 150° F., 150° F. to 160° F., 160° F. to 165° F., 165° F. to 175° F., and 175° F. to 195° F.

In an embodiment, the anaerobic digester effluent is heated using an extended exhaust heat recovery system to further heat treat the effluent and its fibrous solids to Class A pathogen standards.

The hydraulic retention time (HRT) of the effluent in the vessel can be verified according to U.S. EPA standards. HRT may vary, depending on design criteria, from 30 minutes to 48 hours or from 4 hours to 36 hours or from 8 hours to 24 hours or from 12 hours to 16 hours.

The effluent pit 110 will have a gas headspace above the liquid level and below the vessel ceiling, will be air tight, and will be operated under a vacuum. The effluent in the effluent pit will be heated and agitated by the injection of heated gas, including but not limited to air, through injectors or gas nozzles 120. The heated gas will be injected into the liquid near the bottom of the effluent pit, causing a corkscrew mixing effect. Heated air can be supplied by taking ambient air through a cross-flow heat exchanger 122, with the exhaust from the bio-gas engine generator set providing the heated air stream. Heated effluent, agitated with air, will release the majority of the $CO_2$ and some of the $NH_3$ entrained in the liquid waste. Releasing the $CO_2$ from the liquid waste will cause a rise in pH in the liquid waste, increasing the $NH_3$ removal efficiency. The pH value can be used as a marker for how much supersaturated gas has been released. The pH value also can be used as a marker to determine what nutrients can be recovered.

Not to be bound by any particular theory, it is believe that aeration allows for the stripping of super-saturated gases including but not limited to $CO_2$, and that high temperature enhances the kinetics, according to Henry's law, allowing for a more rapid release the supersaturated gases. By aerating the effluent, the pH value is increased and gases, which may interfere with natural flocculation and settling are removed from the liquid effluent.

Additionally, the release of supersaturated gases is tied to the important shifts in chemical equilibria that occur as result of aeration and Henry's Law, such as shifts in carbonate, bicarbonate, and ammonia system equilibria. Aeration allows for the release of supersaturated CO2 but also results in a decrease in total inorganic carbon (carbonates, bicarbonates, etc), which also occurs and leads to more gas release and continued change in pH.

In an embodiment, the aeration rate can be any rate that achieves or assists in the release of supersaturated gases including but not limited to from 2 gallons/cfm to 160 gallons/cfm, or from 5 gallons/cfm to 150 gallons/cfm, or from 10 gallons/cfm to 100 gallons/cfm or from 25 gallons/cfm to 80 gallons/cfm or from 40 gallons/cfm to 50 gallons/cfm. In an embodiment, micro-aeration socks can be used.

In an embodiment, the aeration time can be any amount of time that achieves the release of supersaturated gases including but not limited to from 15 min to 3 days, or from 2 hours to 2 days, or from 4 hours to 24 hours, or from 8 hours to 18 hours, or from 12 hours to 16 hours.

In an embodiment, the aeration rate is selected to allow for stripping of supersaturated gases and maintaining the level of existing struvite or struvite-like colloidal solids. In an embodiment, the aeration rate does not cause or limit dissolution of struvite-like particles, which would release more free phosphates.

In an embodiment, aeration can increase the pH value of the effluent to a desired value including but not limited to 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0 and greater than 12.0. The heating and aeration and the subsequent pH increase effectively eliminates pathogens from the liquid effluent, producing a sterilized liquid.

In another embodiment, the aeration source is designed to produce bubbles of a particular size including but not limited bubbles produced through microaeration, macroaeration, or through the use of different sparger configurations, types, sizes and shapes.

In yet another embodiment, the method comprises prior to aeration of the effluent, separating digested material from the effluent. In yet another embodiment, the method comprises prior to aeration of the effluent, separating digested fibrous material from effluent.

In another embodiment, separating digested material from effluent can be achieved through the use of mechanical methods including but not limited to screens, filters, and column separation.

In one embodiment, the effluent can have large and fine solids. In another embodiment, the effluent can have only fine solids. In still another embodiment, the effluent can have only large solids. In still yet another embodiment, the effluent can comprise in relation to the total solid content in the effluent from 1 to 5% large solids, or from 5 to 10% large solids, or from 10 to 15% large solids, or from 15 to 20% large solids, or from 20 to 25% large solids, or from 25 to 30% large solids, or from 30 to 35% large solids, or from 35 to 40% large solids, or from 40 to 45% large solids, or from 45 to 50% large solids, or from 50 to 55% large solids, or from 55 to 60% large solids, or from 60 to 65% large solids, or from 65 to 70% large solids, or from 70 to 75% large solids, or from 75 to 80% large solids, or from 80 to 85% large solids, or from 85 to 90% large solids, or from 90 to 95% large solids, or from 95 to 99% large solids.

In still yet another embodiment, the effluent can comprise in relation to the total solid content in the effluent from 1 to 5% fine solids, or from 5 to 10% fine solids, or from 10 to 15% fine solids, or from 15 to 20% fine solids, or from 20 to 25% fine solids, or from 25 to 30% fine solids, or from 30 to 35% fine solids, or from 35 to 40% fine solids, or from 40 to 45% fine solids, or from 45 to 50% fine solids, or from 50 to 55% fine solids, or from 55 to 60% fine solids, or from 60 to 65% fine solids, or from 65 to 70% fine solids, or from 70 to 75% fine solids, or from 75 to 80% fine solids, or from 80 to 85% fine solids, or from 85 to 90% fine solids, or from 90 to 95% fine solids, or from 95 to 99% fine solids.

Stripping Tower

The nutrient recovery system also comprises a stripping tower (140). The stripping tower is used for absorbing gaseous ammonia and stabilizing it to ammonium salt solution, which can be more concentrated and easily stored. Briefly, stripping is a distillation procedure that consists of separating fluid components by differences in boiling point or vapor pressure. The usual means of separation is through a column or tower that is packed with one or more various support materials, i.e. Pall Rings, Raschig Rings, Berl Saddles, etc., to increase contact surface. A stripping medium (e.g. hot air or steam, or, in one embodiment, unheated air) is injected into the bottom of the tower and an ammonia containing solution is injected at or near the top. As the ammonia containing liquid trickles down through the packing, it contacts the rising hot vapor and the more volatile ammonia fraction is vaporized and can be collected and further treated. The less volatile liquid component becomes increasingly purer as it nears the bottom of the tower, where it may be collected. U.S. Pat. No. 7,909,995, which issued on Mar. 22, 2011, provides additional information on designs of stripping towers and nutrient recovery systems, and is expressly incorporated herein by reference in its entirety.

The stripping tower is an apparatus that can hold caustic acids including but not limited to sulfuric acid, nitric acid, carbonic acid, hydrochloric acid, and phosphate acid. The stripping towers can also comprise vacuum blowers and pumps.

In one embodiment, the stripping tower can be used to collect any ammonium salt including but not limited to ammonium carbonate, ammonium sulfate, ammonium chloride, ammonium nitrate, and ammonium phosphate.

As opposed to conventional methods that flow manure through stripping towers, plug flow aeration can be employed. This avoids clogging concerns that plaque stripping towers. In addition, conventional stripping towers focus on high efficiency through very high aeration rates. These aeration rates are often associated with pressure drops and high electricity demands.

In one embodiment, ammonia stripping is carried out using a closed loop tower design that uses air as the stripping medium and includes an acid absorption system to capture ammonia as ammonium salt. Air can be used for this process because, although it does not have as high an ammonia absorbance capacity as other potential carrier gases, air is inexpensive and the pH adjustment needed can be maintained at a relatively low level (e.g. pH 10) because the process takes advantage of the hot (about 32-35° C.) manure wastewater coming from the anaerobic digester to compensate.

In one embodiment, a single tower design may be used. A single tower includes waste water input for ammonia stripping and acid input for acid absorption. Air is directed into the bottom of the tower using the fan or blower. Air circulates in an enclosed system, thus allowing for enhanced ammonia recovery and a reduction in energy inputs as the air without outside influence maintains its temperature for a longer period of time. In some embodiments, the air is heated, e.g. to a temperature of about 50° C., or in the range of from about 40° C. to about 60° C.

In an embodiment, the effluent air in the effluent pit 110 will be transferred to a packed stripping tower 140 where a liquid wash of sulfuric acid (or other acid) will drop the pH of the liquid stream (combined liquid wash and effluent air) and create a solution comprising ammonium sulfate. The solution can comprise an ammonium-salt slurry comprising from about 30% to about 60% ammonium sulfate. The ammonium sulfate can be collected and used as fertilizer. In another embodiment, other acids and contact chemicals can be used to produce any number of ammonium salts including but not limited to ammonium nitrate, ammonium phosphate, ammonium citrate, each which can serve as a fertilizer.

In one embodiment, the effluent air, under vacuum, in the effluent pit 110 will be transferred to a packed stripping tower 140.

Solid/Liquid Separator

At the end of the engineered HRT, the sterilized effluent will be pumped to a solids/liquid separator 130; resulting in a separated solids 135 stream that will meet Class A bio-solids criteria and a separator liquid stream 137 that will also be sterilized and pathogen free. In another embodiment, at the end of the engineered HRT, the effluent will be strongly reduced in pathogens.

The separated solids and separated liquid will be reduced in ammonia-N content. The ammonium sulfate created will be a higher-value utilization of the natural ammonium found in organic wastes and will be in a chemical form that is easier to utilize and market. The separated solids can be utilized for animal bedding, horticultural usage, or fertilizer. The removal and capture of ammonia from the liquid effluent also reduces the natural release of ammonia gas into the atmosphere from waste storage and disposal and thus, reduces nox, $N_2O$ and greenhouse gas emissions and the environmental effects associated with ammonia release and these other nitrogen gas releases to the atmosphere.

Air-Tight Vessel

The separator liquid stream, temperature maintained from 130° F. to 180° F. or from 140° F. to 160° F. can be transferred to a single chamber or multi-chamber air-tight vessel. A three chamber air-tight vessel 145 is shown in FIG. 2. The first chamber 150 is separated from the second chamber 160 by a barrier wall. The second chamber 160 is separated from the third chamber 170 by a barrier wall.

In an embodiment, the barrier wall can be made of any suitable material that keeps the chambers distinct including but not limited to plastic PVC, polyethylene, polypropylene, methacrylic or acrylic plastic, fiber glass reinforced plastic (FRP), or stainless steel.

In an embodiment, the first and third chambers can be in any shape or dimension that allows the desired outcome including but not limited to a rectangle, a square, a triangle, a circle, a pentagon and a V-notched shape. One or more pumps can be located at or near the floor of the first and/or third chambers.

a. The First Chamber

The first chamber 150, which may not be utilized in all configurations, will be a "quiet zone" chamber where the separator liquid will be allowed to decant. The large percentage of the minute solids that passed through the solids separator with the liquid effluent likely will settle to the bottom of the first chamber 150 and will be collected and removed for dewatering. Anaerobic digested and aerated liquids with decreased solids content, due to a separation process, and at a higher liquid temperature, separate faster and more efficiently. The liquid stream will plug flow through the first chamber 150, designed with an HRT from 30 minutes to 24 hours or from 60 minutes to 18 hours or from 2 hours to 16 hours or from 4 hours to 12 hours or from 8 hours to 10 hours. The liquid stream will plug flow into the second chamber 160.

b. The Second Chamber

The second chamber 160 can have any desired shape or dimensions that achieve the desired result including but not limited to a rectangle, a square, a circle, a triangle, a pentagon and a V-notched shape.

In the second chamber 160, the liquid stream may be gas-agitated with air that is heated in a heat exchanger with the engine exhaust. Nozzles or jets for injection of air into the second chamber can be located at or near the floor of the second chamber 160. In another embodiment, the liquid stream may be hydraulic-agitated with a recirculation pump, or can be mechanically agitated with a prop agitation system. In an embodiment, the agitation can be for a suitable period of time including but not limited to 30 minutes to 1 hour, 1 hour to 2 hours, 2 hours to 4 hours, 4 hours to 6 hours, 6 hours to 8 hours, 8 hours to 10 hours, 10 hours to 12 hours and greater than 12 hours.

In an embodiment, the liquid stream will have continuous agitation, which will aid in the removal of ammonia if removal is desired.

In one embodiment, a high pH liquid including but not limited to quicklime or a caustic, can be added to the separated liquid stream, upon entering the second chamber, to increase the pH of the liquid effluent to a suitable value including but not limited to 9.0-9.1, 9.1-9.2, 9.2-9.3, 9.3-9.4, 9.4-9.5, 9.5-9.6, 9.6-9.7, 9.7-9.8, 9.8-9.9, 9.9-10.0, 10.0-11.0, 11.0-12.0, 12.0-12.5, and greater than 12.5.

A benefit of decreasing the solids content of a waste liquid is that less lime or caustic or in the case of no caustic addition, less aeration time and rate, is needed to raise the pH of a given volume of liquid, thereby decreasing the chemical treatment cost of the nutrient recovery system. The liquid stream will plug flow through the second chamber 160 of the air-tight vessel 140 as it is agitated utilizing the mixed plug flow (corkscrew) agitation method described above in the section entitled Anaerobic Digesters, and will thereby maintain a consistent HRT in the vessel.

Increasing the pH of an anaerobic digester effluent to a pH of about 9.5 or higher, at a temperature from 110° F. to about 160° F. or greater, will convert soluble ammonium-nitrogen ($NH_4$—N) to non-soluble, volatile ammonia nitrogen ($NH_3$—N). The ammonia-nitrogen 162 will be volatilized rapidly with the continuous agitation provided in the air tight vessel and will be collected in the head space provided in the vessel. Vacuum extraction of the head space gases may be utilized to further increase the volatilization rate inside the air tight vessel. Subsequently, by utilizing a system of air scrubbing the gaseous air stream with a low pH liquid solution of $H_2SO_4$ or similar acidic chemical, in a cross-flow air stripping tower 140, the ammonia will be removed from the air stream and captured as liquid ammonium sulfate. Ammonium sulfate is a highly valuable, easily solid fertilizer utilized by farmers and it will be an income stream for the nutrient removal system. Most importantly, the removal of the ammonium-nitrogen from the liquid waste stream solves one of the major disposal issues of the anaerobic digester effluent: high nitrogen content. In addition, removal of the ammonium-nitrogen also limits the natural discharge of $NH_3$ and $N_2O$ into the atmosphere.

c. Third Chamber

The liquid stream will plug flow into a third chamber 170, a "quiet zone" with no agitation where the liquid will be allowed to decant. The remaining solids will settle to the bottom of the third chamber, where they can be removed by a bottom discharge separation system. By the addition of quicklime, with its high pH and magnesium component, and the high temperature agitation that preceded the third chamber, a high level of magnesium-ammonium-phosphate (struvite) easily and readily settles. The settled solids will be removed from the third chamber 160 and dewatered.

In an embodiment, settling and dewatering of the nutrient rich solids is made easier through the use of a primary pump. In another embodiment, acid can be added to condense the solids layer for decanting.

Magnesium-ammonium-phosphate is also a highly valuable, easily sold fertilizer utilized by farmers and it will also be an income stream for the nutrient removal system. By removing the phosphorus and more ammonium from the liquid waste stream, the two largest disposal issues of the anaerobic digester effluent have been removed. The methods, systems and apparatuses disclosed herein contribute to solving many of the environmental and regulatory issues that generators/disposers of liquid organic wastes encounter in the US.

Heat Exchanger

The decanted liquid with a temperature from 140° F. to 175° F. will be pumped to a waste-to-waste heat exchanger 180 where the temperature from the decanted liquid will be conserved by heating the cool incoming raw organic wastes at the front of the anaerobic digester system 10. This will conserve heat costs in the total system.

The decanted liquid will proceed from the heat exchanger 180 to a cross-flow, packed tower gas scrubbing system 190. In this gas scrubbing tower 190, the high pH decanted liquid will be exposed to the biogas 200 from the anaerobic digester system 10. The anaerobic digester biogas 200 typically has a hydrogen sulfate ($H_2S$) content of 500 ppm or higher and is considered very corrosive to the reciprocating engines utilized to convert the biogas into power for the electrical generation process.

The reaction in the stripping tower 190 of the high pH decanted liquids with the acidic $H_2S$ found in the biogas stream lowers the $H_2S$ level in the biogas to less than 50 ppm. This lower $H_2S$ concentration in the biogas and significantly reduces the operation and maintenance costs of the reciprocating engines in the AD system.

Additionally, the high pH of the decanted liquid is now lowered to approximately 8.0 after neutralizing the acidic $H_2S$ and removing a significant percentage of $CO_2$ from the biogas; resulting in a more friendly-to-use liquid for the farmer/owner and easier liquid disposal options. Other options such as biogas bubbling chamber and micro-diffusers can also be utilized in lieu of a stripping tower.

Figure 3A:
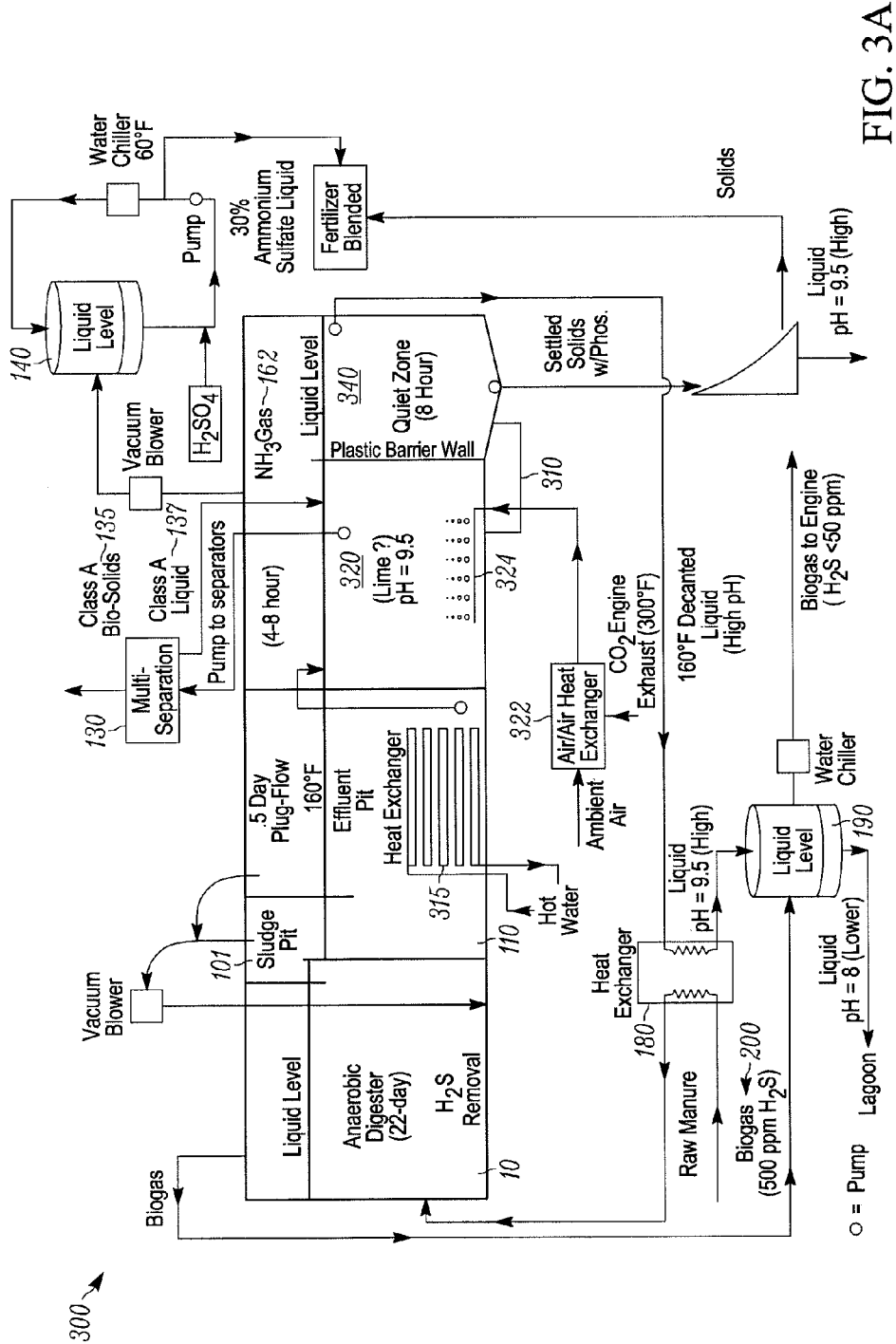
FIG. 3A is a schematic of one embodiment of a nutrient recovery system showing a two-chambered air-tight vessel.

FIG. 3 shows another embodiment of a nutrient recovery system 300. Nutrient recovery system 300 is similar to system 100, with the exception that a two-chamber air tight vessel 310 is shown.

The nutrient recovery system 300 comprises an effluent pit 110 that comprises a heat exchanger 315 to heat the anaerobic digester effluent. The effluent pit also comprises a pump to transport the anaerobic digester effluent into the first chamber 320 of the two-chamber air-tight vessel 310.

The two-chamber air tight vessel 310 has a chamber 320 that allows for the liquid stream to be gas-agitated with air that is heated in a heat exchanger 322 with the engine exhaust. Nozzles or jets 324 for injection of air into chamber 320 can be located at or near the floor of chamber 320. In another embodiment, the liquid stream may be hydraulic-agitated with a recirculation pump, or can be mechanically agitated with a prop agitation system. In an embodiment, the agitation can be for a suitable period of time including but not limited to 30 minutes to 1 hour, 1 hour to 2 hours, 2 hours to 4 hours, 4 hours to 6 hours, 6 hours to 8 hours, 8 hours to 10 hours, 10 hours to 12 hours and greater than 12 hours In an embodiment, the effluent is adjusted to a pH value ranging from 9.0 to 10.5. In an embodiment, a pH value of greater than 9.5 can be achieved by aeration, or aeration and the addition of an agent with a high pH value including by not limited to a caustic or quicklime. The addition of an agent with a high pH value can be used to increase the pH to a value of 9.5-10.0, 10.0-10.5, 10.5-11.0, 11.0-11.5, 11.5-12.0, 12.0-12.5, and greater than 12.5.

The heated and high pH effluent can be pumped to a multi-separator 130 that separates solids 135 from liquids 137, which satisfy the requirements for the liquids and solids to be considered Class A. The liquid effluent is pumped into chamber 340, which is a quite zone. The remaining components, recovery processes, and pH adjustments of the liquid effluent are essentially as described for system 100.

Figure 3B:
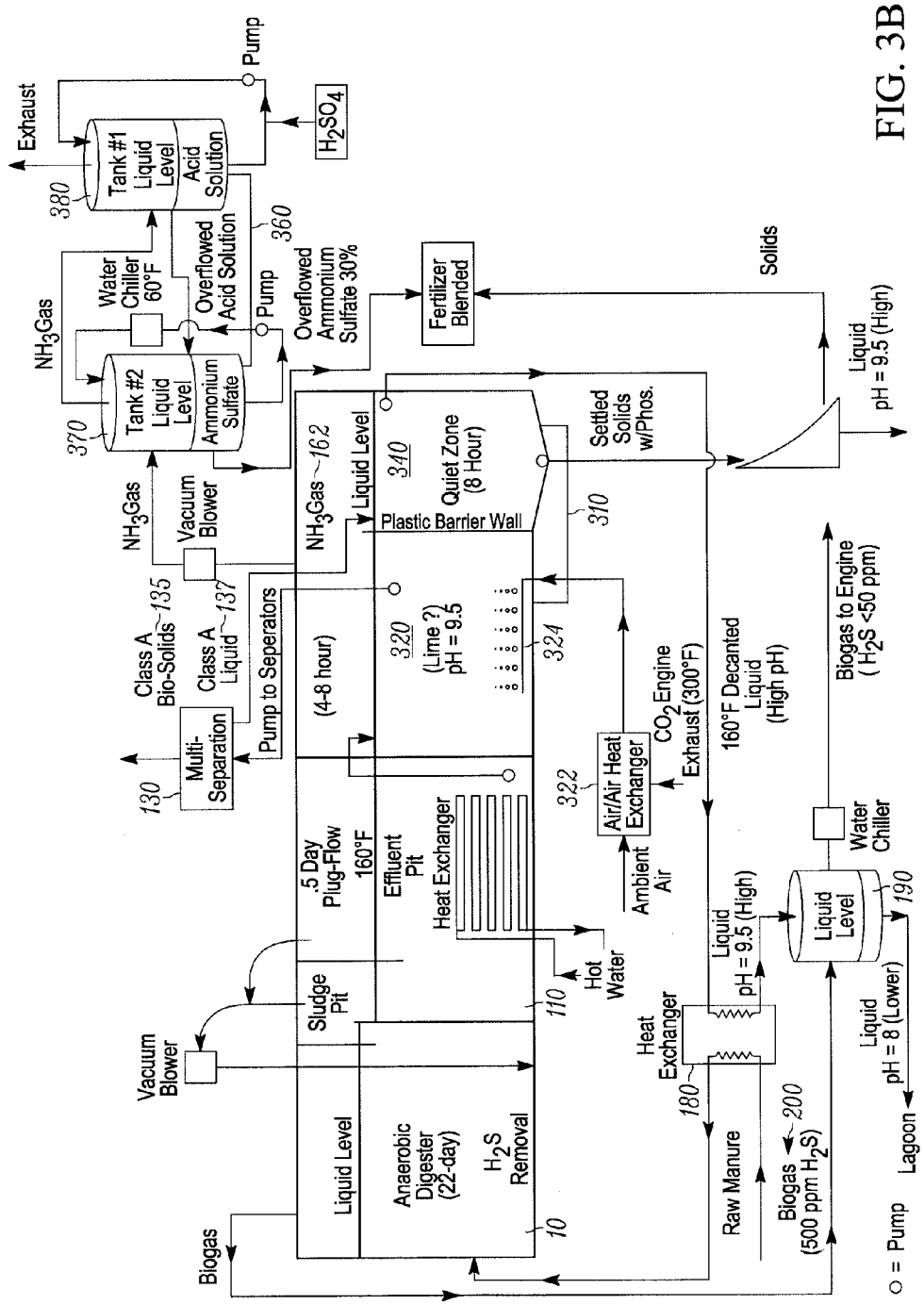
FIG. 3B is a schematic of one embodiment of a nutrient recovery system showing a stripping tower with a two tank system.

FIG. 3B shows another embodiment of a nutrient recovery system 305. Nutrient recovery system 305 is similar to system 300, with the exception that a two acid tower system is used (360). System 305 comprises inter alia an anaerobic digester 10, a sludge pit 101, an effluent pit 110, a separation device, 130, and a two chamber air-tight vessel 310, and a two acid tower system (360).

Anaerobic Digester

Any type of anaerobic digester (10) can be used as described above. In one embodiment, a mixed plug-flow through digester is used. In another embodiment, the digester has a retention time selected from the group consisting of 18, 19, 20, 21, 22, 23, 24, 25, 26, 27, 28, 29, 30, and greater than 30 days.

Effluent Pit

In one embodiment, the anaerobic digester effluent can gravity flow, or it can be pumped, into an insulated effluent pit 110. In essence, the effluent pit is as described for system 100. In one embodiment, $CO_2$ and ammonia from the effluent pit is not pumped to the two acid tower system. Gas is pumped from the head-space of the effluent pit to a vacuum blower and back into the anaerobic digester. The re-circulated gas is used to circulate solids in the anaerobic digester.

In another embodiment, a stainless steel heat exchanger is used to heat the effluent and is supplied by a hot water tank for the digester. The effluent is heated to 160° F. in the effluent pit.

Air-Tight Vessel

The effluent is pumped from the effluent pit to a single chamber or multi-chamber air-tight vessel. A two chamber air-tight vessel 310 is shown in FIG. 3B. The first chamber 320 is separated from the second chamber 340 by a barrier wall.

In an embodiment, the barrier wall can be made of any suitable material that keeps the chambers distinct including but not limited to plastic PVC, polyethylene, polypropylene, methacrylic or acrylic plastic, fiber glass reinforced plastic (FRP), or stainless steel.

In an embodiment, the first and second chambers can be in any shape or dimension that allows the desired outcome including but not limited to a rectangle, a square, a triangle, a circle, a pentagon and a V-notched shape. One or more pumps can be located at or near the floor of the first and/or third chambers.

The First Chamber (320)

The first chamber 320 can have any desired shape or dimensions that achieve the desired result including but not limited to a rectangle, a square, a circle, a triangle, a pentagon and a V-notched shape. The first chamber 320 serves as an aeration reactor.

In the first chamber 320, the anaerobic digester effluent may be gas-agitated with ambient air that is heated in a heat exchanger (322) with the $CO_2$ engine exhaust. Aeration allows for release of the super-saturated gases, which impeded settling. Nozzles or jets (324) for injection of air into the first chamber can be located at or near the floor of the first chamber 320. In another embodiment, the liquid stream may be hydraulic-agitated with a recirculation pump, or can be mechanically agitated with a prop agitation system. In an embodiment, the agitation can be for a suitable period of time including but not limited to 30 minutes to 1 hour, 1 to 2 hours, 2 to 4 hours, 4 to 6 hours, 6 to 8 hours, 8 to 10 hours, 10 to 12 hours, 12-18 hours, 18-24 hours, 24-36 hours, 36-48 hours, 48-60 hours, 60-72 hours and greater than 72 hours.

In an embodiment, the liquid stream will have continuous agitation, which will aid in the removal of ammonia if removal is desired.

In one embodiment, an agent with a high pH value can optionally be added. The agent includes but is not limited to quicklime or a similar caustic. The pH of the liquid effluent can be increased to a suitable value including but not limited to 9.0-9.1, 9.1-9.2, 9.2-9.3, 9.3-9.4, 9.4-9.5, 9.5-9.6, 9.6-9.7, 9.7-9.8, 9.8-9.9, 9.9-10.0, 10.0-11.0, 11.0-12.0, 12.0-12.5, and greater than 12.5.

The liquid stream will plug flow through the first chamber 320 of the air-tight vessel 310 as it is agitated utilizing the mixed plug flow (corkscrew) agitation method described above in the section entitled Anaerobic Digesters, and will thereby maintain a consistent HRT in the vessel.

Increasing the pH of an anaerobic digester effluent to a pH of about 9.5 or higher, at a temperature of 140° F. or greater, will convert soluble ammonium-nitrogen ($NH_4$—N) to non-soluble, volatile ammonia nitrogen ($NH_3$—N). An additional benefit of high temperature and high pH treatment is the pathogen destruction in the liquid. The ammonia-nitrogen 162 will be volatilized rapidly with the continuous agitation provided in the air tight vessel and will be collected in the head space provided in the vessel. Vacuum extraction of the head space gases will be utilized to further increase the volatilization rate inside the air tight vessel.

In another embodiment, the aeration reactor comprises a heat exchanger to heat the air. An air-to-air heat exchanger will scrub hot air coming from the exhaust side of the stripping towers and heat fresh air that will be at ambient temperature. After going through the air-to-air heat exchanger the hot air will go through a roots-style blower (also increasing the air temperature) and be pumped to the diffusers in the aeration tank. A mixing valve is installed between the blower and the air-to-air heat exchanger that will operate off of a temperature probe that is downstream of the blower. This mixing valve will allow the air-to-air exchanger to be bypassed when the air is too hot to be supplied to the diffusers.

In another embodiment, condensation in the ammonia gas that comes out of the aeration tank is controlled by insulating the gas line between the aeration tank and the stripping towers. In addition, the stripping towers can be insulated as well as the gas line from the stripping tower to the air-to-air heat exchanger. In another embodiment, the gas line can be designed to slope toward the aeration tank before going straight down into the stripping tower. This design will help to ensure that if there is any condensation, it ends up back in the aeration tank and not the stripping towers.

Solid/Liquid Separator

At the end of the engineered HRT, the anaerobic digester effluent will be pumped from the first chamber (320) to a solids/liquid separator 130; resulting in a separated solids 135 stream that will meet Class A bio-solids criteria and a separator liquid stream 137 that will also be sterilized and pathogen free. The separated solids and separated liquid will be reduced in ammonia-N content. The ammonium sulfate created will be a higher-value utilization of the natural ammonium found in organic wastes and will be in a chemical form that is easier to utilize and market. The separated solids can be utilized for animal bedding, horticultural usage, or fertilizer. The Class A liquid is pumped back into the head-space of the air-tight vessel (310).

Two Tower Stripping System

The system that is used for ammonia stripping may be of any suitable design. For example, a two-tower system may be used. In the two tower system, a first tower is used for ammonia stripping. The waste water effluent is injected near the top of the first tower. Air is directed into the bottom of the first tower using a fan or blower. The air accumulates volatilized ammonia and, with the pressures developed by the fan or blower, is sent to the bottom of the second tower. This ammonia enriched air is blown upward as acid is sent from the top of the second tower down through the media, absorbing the ammonia from the air. The resulting air, now ammonia free is returned back to the bottom of the first tower for continuation of the process. In this example, the acid injected into the second tower is sulfuric acid but it can be any acid that can combine with ammonia to form an ammonia salt In one embodiment, heat is supplied by excess generator heat from the AD process. However, in a preferred embodiment of the invention, the air is not directly heated, but instead is indirectly heated through the continual input of 30-35° C. manure wastewater coming from the anaerobic digester process, and is re-circulated and re-used continually. The air enters the bottom of the stripping section and flows upward, absorbing gaseous ammonia while moving toward the top of the ammonia stripping section of the tower. The action of the flow coupled with the use of a blower or fan sends the ammonia saturated air into an acid section of the tower. In one embodiment, the acid section contains sulfuric acid and, as the ammonia saturated air flows through the acid, the ammonia reacts with the acid to form an ammonium sulfate solution, which is removed. The resulting ammonia depleted air is then circulated back to the stripping section to accumulate additional ammonia, and so on. The result is a continuous, closed system whereby the same air can continually be used to absorb and release ammonia over and over again, resulting in significant cost savings in regard to electricity and heating.

Conventional ammonia stripping systems are not designed to deal with the usual amount of solid matter in an anaerobic digester effluent. Whereas the acid absorption tower (two-tower system) or the acid absorption portion of the tower in a single tower system may employ conventional small packing material in order to take advantage of its high efficiency, the anaerobic digester effluent may tend to clog small packing material in the ammonia stripping section. The stripping towers described herein may therefore be specially designed to solve this problem, and the tower design may be tailored to accommodate the particular type of animal waste that is being treated.

In one embodiment, a traditional tower is used but it is packed with coarse packing material and a relatively short packing height is used. For example, a tower with an inner diameter of 4" with a 1" pall ring and a packing height of 5' may be utilized with a feed flow of up to at least about 10 g/L of TS. In general, plastic packing material with a nominal diameter no less than 2" and a specific area of 80-120 $m^2/m^3$ may be used. Although smaller packing material or packing material with higher specific surface area will be better for mass transfer, it will be more easily clogged. A lower packing height (3-5 m) compared with the conventional 6.1-7.6 m is also preferred in order to reduce clogging.

In another embodiment, a tray tower with specially designed anti-clogging trays may be employed. The tray can be substantially flat and contain one or more gas guiding holes, and, optionally, one or more additional holes, which permit the flow of air and liquid through various trays. The gas guiding holes include a spaced apart cover that protects against the packing material in the tower from sealing off the gas guiding holes. Furthermore, the cover is opened in a direction desired for movement of gas and liquid. The tray may be of any suitable shape for example, substantially round, square etc. so long as the trays properly fit into and can be stably attached within the tray tower.

In one embodiment, the stripping tower is used in conjunction with an effluent pit, which comprises a single basin that does not use trays or media. With the use of a single basin, there is no concern with regard to clogging.

Returning now to FIG. 3B, $NH_3$ gas (162) in the head space of the air-tight vessel (310) will be piped to a two-tower acid system (360), where controlled amounts of sulfuric acid make contact with ammonia in the air and produce dissolved ammonia sulfate bio-fertilizer. $NH_3$ gas (162) is piped into tank two (370) of the two-tower system (360). Sulfuric acid is pumped into tank 1 (380) of the two tower system (360). Overflow acid solution is piped into tank two (370), which is mixed with $NH_3$ gas from the overhead space of the airtight vessel (310). Residual $NH_3$ gas is piped into tank 1 (380), and the circuit continues with overflow acid solution piped back into tank 2 (370). In this example, sulfuric acid is used but as discussed above, numerous types of acids can be used. The sulfuric acid will drop the pH of the air stream and create a solution comprising ammonium sulfate. The solution can comprise a ammonium-salt slurry comprising from about 30% to about 60% ammonium sulfate. The ammonium sulfate can be collected and used as fertilizer. The ammonium salt generated will depend on the acid used. For clarity, sulfuric acid is used in this example, but as stated previously, any suitable acid can be used, which will produce an appropriate ammonium salt.

Subsequently, by utilizing a system of air scrubbing the gaseous air stream with a low pH liquid solution of $H_2SO_4$ or similar acidic chemical, in a cross-flow two tower acid system 360, the ammonia will be removed from the air stream and captured as liquid ammonium sulfate. Ammonium sulfate is a highly valuable, easily solid fertilizer utilized by farmers and it will be an income stream for the nutrient removal system. Most importantly, the removal of the ammonium-nitrogen from the liquid waste stream solves one of the major disposal issues of the anaerobic digester effluent and detrimental gaseous N-products into the atmosphere.

Traditionally, a single acid contact tower is used to recirculate fresh acid/solution on a pH controller to produce an overflow product that is ammonium sulfate with a low pH (~2). In the embodiments disclosed herein, a two tower approach allows the ammonia itself (and its high pH) to moderate the final overflow liquids pH. The final overflow pH can be kept at pH 7 or any other pH desired for final product sales.

In another embodiment, spray bars on a pressure control meter can be used to add water so that the concentration is held constant at saturation but not above. This helps to avoid inconsistent or low N product. In addition, it helps to prevent crystallization and clogging of the tower.

In another embodiment, filters can be used to clean any residual organics to make a clear solution.

The Second Chamber

The liquid stream will plug flow into a second chamber 340, a "quiet zone" with no agitation where the liquid will be allowed to decant. The remaining solids will settle to the bottom of the second chamber, where they will be removed by a bottom discharge separation system. The aeration and high temperature that preceded the second chamber produces a high level of solids such as calcium and magnesium bound phosphates, and magnesium-ammonium-phosphate, which easily and readily settles. The settled solids will be removed from the second chamber 340 and dewatered.

In an embodiment, settling and dewatering of the nutrient rich solids is made easier through the use of a primary pump. In another embodiment, acid can be added to condense the solids layer for decanting.

Magnesium-ammonium-phosphate is also a highly valuable, easily sold fertilizer utilized by farmers and it will also be an income stream for the nutrient removal system. By removing the phosphorus and more ammonium from the liquid waste stream, the two largest disposal issues of the anaerobic digester effluent have been removed. The methods, systems and apparatuses disclosed herein contribute to solving many of the environmental and regulatory issues that generators/disposers of liquid organic wastes encounter in the US.

The remaining components including the heat exchanger of the nutrient recovery system 305 are as described for nutrient recovery system 100.

Reactor for Removal of Contaminants from Biogas

The system 10 also includes a reactor for the removal of contaminants such as $H_2S$ (7) in the biogas. In one embodiment, the same reactor can be used to remove $CO_2$ from the biogas. In another embodiment, a separate reactor can be used to remove $CO_2$ from the biogas.

In one embodiment, the alkaline effluent, which is produced continuously on-site as a byproduct of the anaerobic digestion and the nutrient recovery process, is used as an absorbent to remove $H_2S$, and some $CO_2$, from the biogas. At the same time, the pH of the anaerobic digester effluent will be returned to near neutrality (pH<7.5) (Zhao, Dvorak et al. 2012). Such an approach will eliminate the cost of purchasing expensive alkaline solvents (e.g. NaOH, CaO) and eliminate the need of a regeneration process.

In another embodiment, after removing $H_2S$, the effluent can be regenerated to produce an effluent with an alkaline pH and can be used to remove $CO_2$ from the biogas. The effluent can be regenerated by aeration. Any effluent from the manure management lifecycle can be regenerated and used to remove $CO_2$ from the biogas.

Any reactor may be used that allows contact between the biogas and the alkaline effluent. Contact protocols include, but are not limited to: direct contacting protocols, e.g., bubbling the gas through the volume of effluent, concurrent contacting means, i.e., contact between unidirectionally flowing gaseous and liquid phase streams, countercurrent means, i.e., contact between oppositely flowing gaseous and liquid phase streams, and the like. The gaseous stream may contact the effluent source vertically, horizontally, or at some other angle. The biogas may be contacted with the effluent source from one or more of the following positions: below, above, or at the surface level.

Contact may be accomplished through the use of infusers, bubblers, fluidic Venturi reactor, sparger, airstone sprager, inlet orifice sprager, gas filter, spray, tray, catalytic bubble column reactors, draft-tube type reactors or packed column reactors, and the like, as may be convenient. Where desired, two or more different biogas charging reactors (such as columns or other types of reactor configurations) may be employed, e.g., in series, such as three or more, four or more, etc.

In certain embodiments, various means, e.g., mechanical stirring, electromagnetic stirring, spinners, shakers, vibrators, blowers, ultrasonication, to agitate or stir the reaction solution are used to increase the contact between the biogas and the alkaline effluent.

In one embodiment, packed beds may be used with the alkaline effluent for the absorption of $H_2S$ over $CO_2$. In one embodiment, filters and straining mechanisms are used with the packed beds to prevent clogging.

In one embodiment, the reactor is designed to selectively and preferentially separate $H_2S$ first from a rich $CO_2$ biogas through unique engineering design of the reactor. In a subsequent step or reaction, the reactor is designed to remove the $CO_2$ in the biogas.

In another embodiment, the reactor has an effluent height selected from the group consisting of: 0.030-0.070, 0.070-0.1, 0.1-0.15, 0.15-0.30, 0.30-0.45, 0.45-0.60, 0.60-0.8, 0.8-1, 1-3, 3-5, 5-7, 7-9, 9-11, 11-13, 13-15, 15-17, 17-20, 20-25, 25-50, 50-100, 100-150 and greater than 150 meters.

In another embodiment, the reactor may have a sparger. Any sparger can be used including but is not limited to airstone, single inlet orifice, macro and micro-diffuser and a multi-site inlet orifice.

In another embodiment, the reactor can have one or more gas spargers that produces small bubbles including but not limited to perforated plate, porous plate, membrane, ring type sparger and arm spargers. In another embodiment, the reactor can have one or more spargers that produce large bubbles.

In another embodiment, any number of contact towers allowing for contact of liquid and gas to occur while controlling contact time in unique ways to allow for preferential performance will work.

In another embodiment, the reactor has a gas:liquid ratio selected from the group consisting of: 20:1, 21:1, 22:1, 23:1, 24:1, 25:1, 26:1, 27:1, 28:1, 29:1, and 30:1. In one embodiment, the reactor has a gas:liquid ratio of 21-25:1.

In one embodiment, the reactor comprise pipes and tubing for transporting the effluent and biogas. The reactor can comprise pumps for transporting the effluent and biogas. In addition, the reactor can comprise meters for controlling the flow rate of the effluent and biogas.

In another embodiment, the reactor can have a gas sampling port so the treated and untreated biogas can be analyzed. The reactor can comprise a rotameter for flow rate control into reactor. The reactor can comprise a peristaltic pump for inserting effluent into the reactor. The reactor also can comprise online pH probes that connect to a computer to measure the pH of the effluent. The reactor also can have a liquid sampling port so the effluent can be removed and analyzed. As discussed above, the reactor can also have one or more gas infusers, or spargers. In one embodiment, the reactor may have one or more airstone spragers. In another embodiment, the reactor may have one or more inlet orifice sparger.

A. Bubble Columns

In one embodiment, a bubble column may be used as an absorption apparatus to remove contaminants from biogas. Bubble columns offer several advantages including ease of construction, lack of moving parts and maintenance, excellent heat and mass transfer characteristics, and the ability to handle solid particles without clogging equipment (Kantarci, Borak et al. 2005; Green and Perry 2008).

Figure 4:
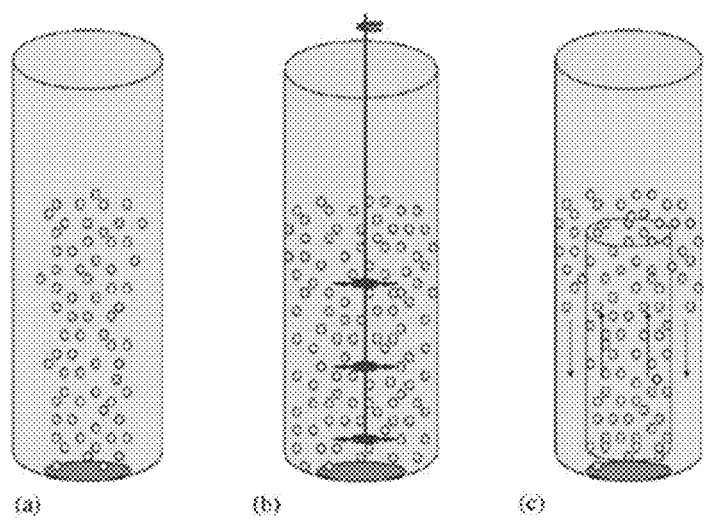
FIG. 4 is a schematic of a bubble column in different configurations. The schematic labeled (a) represent a bubble column reactor. The schematic labeled (b) represents an aerated stirred reactor. The schematic labeled (c) represents an air-lift reactor.
Figure 5:
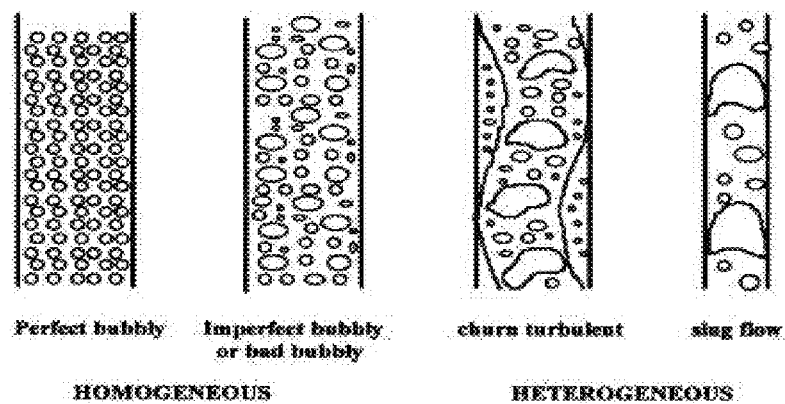
FIG. 5 is a schematic depicting possible flow regimes in bubble columns.

In one embodiment, the bubble column can operate in any acceptable mode. FIG. 4 illustrates a simple bubble column operating in a continuous countercurrent mode of operation. However, other modes of operation can be used.

The raw biogas is fed in from the bottom of the reactor and the alkaline effluent is fed from the top. In one embodiment, the operation can take place at ambient temperature and pressure.

In another embodiment, a lower temperature can be used to aid in $H_2S$ absorption (Wallin and Olausson 1993). In one embodiment, the temperature used for removal of H2S is selected from the group consisting of: 12-15° C., 15-17° C., 17-20° C., 20-22° C., 22-24° C., 24-25° C., 25-27° C., 27-29° C., 29-30° C., 30-32° C., 32-35° C., 35-37° C., 37-39° C., 39-41° C., and 41-43° C.

In another embodiment, the bubble column may have a sparger. Any sparger can be used including but is not limited to airstone, single inlet orifice, macro and micro-diffuser and a multi-site inlet orifice.

In another embodiment, sparger is located at the bottom of the reactor or bubble column. One or more than one sparger, including but not limited to 2, 3, 4, 5, 6, 7, 8, and more than 8, can be used. The spargers may be located in proximity to one another or at a distance from one another.

In another embodiment, the alkaline effluent can be injected at the top of the column. A peristaltic pump can be used to insert the alkaline effluent into the reactor. In one embodiment, the bubble column will be coupled to the nutrient recovery system. The bubble column can be coupled, directly or indirectly, to the nutrient recovery system.

In one embodiment, the bubble column can operate in any mode of operation including but not limited to semi-continuous (continuous in the gas phase but batch with respect to the liquid phase), continuous in both phases in either a countercurrent or co-current mode of operation. Furthermore, the configurations of the liquid flow can be altered in a variety of ways. One such bubble column, airlift loop reactor, incorporates risers and down corners to promote enhanced mixing between gas and liquid.

An important component of a bubble column is its flow regime because of its significant effect on operation and performance (Kantarci, Borak et al. 2005).

In one embodiment, the bubble column may have any flow regimes presented in the literature including but not limited to: homogenous (bubbly flow), heterogeneous (churn-turbulent), and slug flow (Hyndman, Larachi et al. 1997). The flow regimes are determined by numerous factors including but not limited to the superficial gas velocity, column diameter, liquid and gas phase properties, and distributor design (Shaikh and Al-Dahhan 2007).

The homogenous regime, which is characterized by small uniform bubbles and small rise velocities, is encountered at superficial velocities approximately below 5 cm/s in a medium similar to water at low viscosity (Deckwer and Field 1992). In the bubbly flow regime, there is no coalescence or breakup of bubbles (Thorat and Joshi 2004).

The heterogeneous churn-turbulent regime is characterized by the existence of large and small bubbles due to coalescence and breakup. Due to this breakup and coalescence, a wide range of bubble sizes are found in the heterogeneous regime ranging from a few millimeters for the smaller bubbles, to a few centimeters for the larger bubbles (Matsuura and Fan 1984). In addition, intensification in turbulence occurs in heterogeneous regimes due to the development of liquid circulation patterns, upward in the central region and downward at the walls (Thorat and Joshi 2004). The large bubbles encountered during this regime move in the axial and radial direction, which is why they are referred to as churn-turbulent (Shaikh and Al-Dahhan 2007). Slug flow regimes occur at high superficial velocities and mainly in laboratory scale reactors that have small diameters. The name is given because of the formation of slug cap bubbles. Large bubbles form and their size is dictated by the diameter of the bubble column since the bubbles are stabilized by the column walls (Kantarci, Borak et al. 2005).

One of the most important parameters, mentioned earlier, is the dimensionless gas holdup, which is created by the gas being sparged through the liquid. It is defined as the fraction of the total volume of the system occupied by the gas bubbles (Jamialahmadi and Müuller-Steinhagen 1993). The importance of the gas holdup is its interconnection with the interfacial area created by the bubbles as well as the mass transfer rate between the gas and liquid phases (Jamialahmadi and Müuller-Steinhagen 1993). Factors that influence the gas holdup in bubble columns are the following: superficial gas velocity ($U_g$), liquid properties, column dimensions, operating temperature and pressure, gas distributor design, and solid phase (Kantarci, Borak et al. 2005). Gas holdup increases with increasing superficial velocity and increases with gas spargers that produce small bubbles (e.g. perforated plate, porous plate, membrane, ring type sparger and arm spargers) compared to spargers that produce large bubbles (Jamialahmadi and Müuller-Steinhagen 1993; Bouaifi, Hebrard et al. 2001).

In another embodiment, the bubble column reactor has a gas:liquid ratio selected from the group consisting of: 20:1, 21:1, 22:1, 23:1, 24:1, 25:1, 26:1, 27:1, 28:1, 29:1, and 30:1.

Methods for Removing $H_2S$ from Biogas

In one embodiment, the disclosure relates to a method of removing $H_2S$ from biogas. In another embodiment, the disclosure relates to a method of selectively removing $H_2S$ over $CO_2$ in biogas.

In another embodiment, the disclosure relates to a method comprising using an alkaline effluent to remove $H_2S$ in biogas. In still another embodiment, the disclosure relates to a method comprising using an alkaline effluent to selectively remove $H_2S$ over $CO_2$ in biogas.

In still another embodiment, the disclosure relates to a method comprising using an alkaline effluent from an anaerobic digester to remove $H_2S$ in biogas. In still another embodiment, the disclosure relates to a method comprising using an alkaline effluent from an anaerobic digester to selectively remove $H_2S$ over $CO_2$ in biogas.

In still another embodiment, the disclosure relates to a method comprising using an alkaline effluent produced as a by-product of anaerobic digestion and nutrient recovery process to remove $H_2S$ in biogas. In still another embodiment, the disclosure relates to a method comprising using an alkaline effluent produced as a by-product of anaerobic digestion and nutrient recovery process to remove $H_2S$ in biogas.

In still another embodiment, the disclosure relates to a method comprising treating biogas with an alkaline effluent to remove $H_2S$ in the biogas. In still another embodiment, the disclosure relates to a method comprising treating biogas with an alkaline effluent to reduce the amount of $H_2S$ in the biogas as compared to the staring biogas.

In yet another embodiment, the disclosure relates to a method comprising treating, contacting or sparging biogas into an alkaline effluent to remove $H_2S$ in the biogas. In still another embodiment, the disclosure relates to a method comprising contacting an alkaline effluent with biogas to remove $H_2S$ in the biogas. The biogas can be injected, dispersed, bubbled, sparged, or streamed into the effluent.

In another embodiment, methods disclosed herein can reduce the amount of $H_2S$ in the biogas from 5-10%, or from 10-15%, or from 15-20%, or from 20-25%, or from 25% to 30%, or from 30-35%, or from 35-40%, or from 40-45%, or from 45-50%, or from 50-55%, or from 55-60%, or from 60-65%, or from 65-70%, or from 70-75%, or from 75-80%, or from 80-85%, or from 85-90%, or from 90-95%, or from 95-100%, or from 100-125%, or from 125-150% or from 150-200% as compared to amount of $H_2S$ in the starting biogas.

In another embodiment, the disclosure relates to a method comprising: (a) heating and aerating anaerobic digester effluent in an aeration reactor to produce an alkaline effluent; (b) contacting biogas with the alkaline effluent; and (c) recovering biogas with a reduced amount of $H_2S$ as compared to the starting biogas. In another embodiment, contacting the biogas and the liquid effluent can occur in any suitable vessel. In one embodiment, the vessel is a bubble column.

In another embodiment, the disclosure relates to a method comprising: (a) heating and aerating anaerobic digester effluent in an aeration reactor to produce an alkaline effluent; (b) sparging or injecting biogas into the alkaline effluent to produce treated biogas; and (c) recovering treated biogas with a reduced amount of $H_2S$ as compared to the starting biogas. In another embodiment, contacting the biogas and the liquid effluent can occur in any suitable vessel. In one embodiment, the vessel is a bubble column.

In another embodiment, the disclosure relates to a method comprising: (a) sparging or injecting biogas into an alkaline effluent to produce treated biogas; and (b) recovering treated biogas with a reduced amount of $H_2S$ as compared to the starting biogas. In another embodiment, contacting the biogas and the liquid effluent can occur in any suitable vessel. In one embodiment, the vessel is a bubble column.

In yet another embodiment, the disclosure relates to a method comprising: (a) heating and aerating anaerobic digester effluent in an aeration reactor to produce an alkaline effluent; (b) contacting the alkaline effluent with biogas to produce an effluent with a lower pH and a biogas with a reduced amount of $H_2S$. In one embodiment, the effluent with the lower pH can be used as a fertilizer. In still another embodiment, the biogas with a reduced amount of $H_2S$ can be used for electricity or fuel.

In still another embodiment, the disclosure relates to a method comprising: (a) anaerobically digesting waste material to produce an effluent; (b) heating and aerating anaerobic digester effluent in an aeration reactor to produce an alkaline effluent; (c) contacting biogas with the alkaline effluent to produce an effluent with a lower pH and a biogas with a reduced amount of $H_2S$ as compared to the starting biogas. In another embodiment, contacting biogas with alkaline effluent occurs in a bioreactor.

In another embodiment, the disclosure relates to a method comprising: (a) providing biogas to a bubble reactor; and (b) treating the biogas in the bubble reactor with an alkaline effluent to selectively remove $H_2S$ over $CO_2$ in the biogas.

In one embodiment, the biogas has a gas velocity selected from the group consisting of: 0.0015-0.0025 m·s$^{-1}$, 0.0025-0.0037 m·s$^{-1}$, 0.0037-0.0047 m·s$^{-1}$, 0.0047-0.0057 m·s$^{-1}$, 0.0057-0.0067 m·s$^{-1}$, 0.0067-0.0077 m·s$^{-1}$, 0.0077-0.0087 m·s$^{-1}$, 0.0087-0.0097 m·s$^{-1}$, 0.0097-0.0100 m·s$^{-1}$, 0.01-0.02 m·s$^{-1}$, 0.02-0.04 m·s$^{-1}$, 0.04-0.06 m·s$^{-1}$, 0.06-0.08 m·s$^{-1}$, 0.08-0.1 m·s$^{-1}$, 0.1-0.2 m·s$^{-1}$, 0.2-0.4 m·s$^{-1}$, 0.4-0.6 m·s$^{-1}$, 0.6-0.8 m·s$^{-1}$, 0.8-1.0 m·s$^{-1}$, 1-2 m·s$^{-1}$, 2-4 m·s$^{-1}$, 4-6 m·s$^{-1}$, 6-8 m·s$^{-1}$, 8-10 m·s$^{-1}$ and greater than 10 m·s$^{-1}$.

In another embodiment, the biogas has a flow rate selected from the group consisting of: 0.01-0.03 L/min, 0.03-0.06 L/min, 0.06-0.07 L/min, 0.07-0.08 L/min, 0.08-0.10 L/min, 0.10-0.12 L/min, 0.12-0.13 L/min, 0.13-0.15 L/min, 0.15-0.20 L/min, 0.20-0.25 L/min, 0.25-0.5 L/min, 0.5-0.75 L/min, 0.75-1.0 L/min, 1.0-1.5 L/min, 1.5-2.0 L/min, 2.0-2.5 L/min. 2.5-3 L/min, 3.0-3.5 L/min, 3.5-4.0 L/min. 4.0-4.5 L/min. 4.5-5.0 L/min. 5.0-5.5 L/min, 5.5-6.5 L/min, 6.5-7.5 L/min, 7.5-8.5 L/min, 8.5-9.5 L/min, 9.5-12.0 L/min, 12-15 L/min, 15-25 L/min, 25-35 L/min. 35-45 L/min, 45-55 L/min, 55-65 L/min, 65-75 L/min, 75-85 L/min, 85-95 L/min, 95-105 L/min, 105-115 L/min, and greater than 115 L/min.

In yet another embodiment, the effluent has a flow rate selected from the group consisting of: 0.01-0.03 L/min, 0.03-0.06 L/min, 0.06-0.07 L/min, 0.07-0.08 L/min, 0.08-0.10 L/min, 0.10-0.12 L/min, 0.12-0.13 L/min, 0.13-0.15 L/min, 0.15-0.20 L/min, 0.20-0.25 L/min, 0.25-0.5 L/min, 0.5-0.75 L/min, 0.75-1.0 L/min, 1.0-1.5 L/min, 1.5-2.0 L/min, 2.0-2.5 L/min. 2.5-3 L/min, 3.0-3.5 L/min, 3.5-4.0 L/min. 4.0-4.5 L/min. 4.5-5.0 L/min. 5.0-5.5 L/min, 5.5-6.5 L/min, 6.5-7.5 L/min, 7.5-8.5 L/min, 8.5-9.5 L/min, 9.5-12.0 L/min, 12-15 L/min, 15-25 L/min, 25-35 L/min. 35-45 L/min, 45-55 L/min, 55-65 L/min, 65-75 L/min, 75-85 L/min, 85-95 L/min, 95-105 L/min, 105-115 L/min, and greater than 115 L/min.

Both species, $CO_2$ and $H_2S$, have similar diffusivity's in water with $H_2S$'s solubility only about three times greater than $CO_2$ in water. With such similar physical properties, mass transfer becomes a particularly important factor to selectively remove $H_2S$ over $CO_2$.

In the majority of applications where a bubble column is utilized, the gas-side mass transfer can be regarded as negligible (Kantarci, Borak et al. 2005). Unfortunately, $H_2S$ has been found to have a dominant gas-side resistance to mass transfer and therefore cannot be considered negligible (Garner, Long et al. 1958; Bendall, Aiken et al. 1983; Yih and Sun 1987; Srinivasan and Aiken 1988). This is why most selective $H_2S$ purification is performed in an absorption apparatus that favors a gas-film controlled process (e.g. packed bed) (Wallin and Olausson 1993).

However, $CO_2$ has dominant resistance to mass transfer on the liquid-side, which can be exploited in a bubble column. This resistance can be attributed to $CO_2$ having a slow initial reaction in solution, which is not the case when $H_2S$ dissociates in a solution. The following reactions take place with $H_2S$ and water at 25° C. (Sun, Nesic et al. 2008)

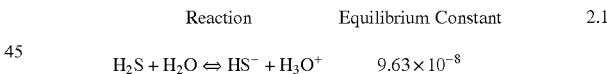

| Reaction | Equilibrium Constant | 2.1 |
|---|---|---|
| $H_2S + H_2O \Leftrightarrow HS^- + H_3O^+$ | $9.63 \times 10^{-8}$ | |

The reaction taking place with $H_2S$ and $H_2O$ can be regarded as instantaneous and therefore equilibrium is assumed. On the other hand, the hydration reaction taking place between $CO_2$ and water is a reversible slow reaction, followed by fast reactions at 25° C. (Meldon, Stroeve et al. 1982):

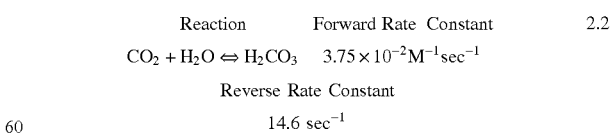

| Reaction | Forward Rate Constant | 2.2 |
|---|---|---|
| $CO_2 + H_2O \Leftrightarrow H_2CO_3$ | $3.75 \times 10^{-2} M^{-1} sec^{-1}$ | |
| | Reverse Rate Constant | |
| | $14.6 \ sec^{-1}$ | |

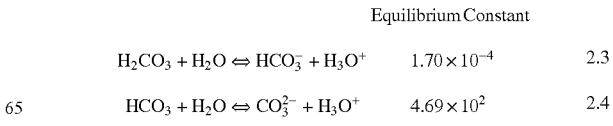

| | Equilibrium Constant | |
|---|---|---|
| $H_2CO_3 + H_2O \Leftrightarrow HCO_3^- + H_3O^+$ | $1.70 \times 10^{-4}$ | 2.3 |
| $HCO_3 + H_2O \Leftrightarrow CO_3^{2-} + H_3O^+$ | $4.69 \times 10^2$ | 2.4 |

Reaction 2.2 is much slower than reaction 2.1 and because of this natural difference in reaction kinetics, $H_2S$ will disassociate into solution much faster than $CO_2$. This will occur regardless of the absorption apparatus chosen for the removal of $H_2S$ over $CO_2$. Some apparatuses have the ability to take further advantage of this difference and improve the selective absorption of $H_2S$ over $CO_2$ by manipulating the gas and liquid film thickness (Kulprathipanja 2002). One way to achieve this is by the use of packing material that can increase the surface area for enhanced mass transfer. Unfortunately, it is not easy to control or manipulate the film thickness in bubbles, but since there is a natural difference in each species' kinetics there should be ways to benefit one over the other in a bubble column by controlling the overall mass transfer from gas to liquid. The selective removal of $H_2S$ over $CO_2$ should increase in a bubble column by decreasing the overall mass transfer of $CO_2$ to limit reactions 2.3 and 2.4 from attributing to the pH reduction of the effluent. The pH directly affects whether $H_2S$ will absorb into the liquid as a physicochemical process, where at a pH below 9, the absorbed $H_2S$ will no longer exist as $HS^-$ in the bulk liquid (Wallin and Olausson 1993). If $CO_2$ is limited from attributing to the pH of the alkaline effluent, then $H_2S$ will have a longer time to absorb into solution before re-emission as gaseous $H_2S$ and as a result increase the amount of biogas that can be purified of $H_2S$.

Decreasing mass transfer can be accomplished in a bubble column by decreasing the gas holdup, $\epsilon_g$, and increasing the bubble diameter, d. One of the most important parameters for bubble columns, the dimensionless $\epsilon_g$ is created by gas being sparged through the liquid and is defined as the fraction of the total volume of the system occupied by the gas bubbles (Jamialahmadi and Müuller-Steinhagen 1993). The importance of the gas holdup is its role in determining the interfacial area, a, created by the bubbles as well as the overall mass transfer rates between the gas and liquid phases (Jamialahmadi and Müuller-Steinhagen 1993). If spherical bubbles are assumed, the specific gas-liquid interfacial area, $a_s$ ($cm^{-1}$), is directly proportional to the gas holdup and inversely proportional to the sauter mean bubble diameter, $d_s$ (cm), by the following equation (Kantarci, Borak et al. 2005):

$$a_s = \frac{6\epsilon_g}{d_s} \quad 2.5$$

The interfacial area is often coupled with the liquid-side mass transfer coefficient to give an overall mass transfer rate per unit volume, $k_L a$ ($s^{-1}$) (Kantarci, Borak et al. 2005). If the gas holdup can be decreased by limiting the amount of bubbles occupying the liquid and the bubble size is increased by increasing the orifice size, the interfacial area will decrease and allow less mass transfer to occur; ultimately decreasing $k_L a$ for both $CO_2$ and $H_2S$.

Factors that influence the gas holdup in bubble columns have been found to include the superficial gas velocity ($U_g$) ($cm \cdot s^{-1}$) (Shah, Kelkar et al. 1982), liquid properties (Li and Prakash 1997), column dimensions (Shah, Kelkar et al. 1982), operating temperature and pressure, gas distributor design (Bouaifi, Hebrard et al. 2001), and solid phase (Krishna, Swart et al. 1997). Gas holdup has been shown to increase when using gas spargers that produce small bubbles, like for example, a perforated plate, porous plate, membrane, ring type sparger and arm spargers compared to spargers that produce larger bubbles (Jamialahmadi and Müuller-Steinhagen 1993; Bouaifi, Hebrard et al. 2001). Since the gas distributor design is relatively easy to manipulate and has a significant effect on the interfacial area it is worthwhile to investigate if the gas distributor can influence the selectivity of $H_2S$ over $CO_2$.

Other parameters that have been found to enhance selectivity in alkaline solutions are the following: low temperature (Yih and Sun 1987), high gas flow rate, and pH of 9-12 (Wallin and Olausson 1993). The temperature of the effluent coming out of the nutrient recovery process is around 50° C., but, after liquid solid separation the temperature will drop to around 15-20° C., which should help the absorption of $H_2S$. The pH of the effluent coming out of the $NH_3$ stripping process depends on the amount of $CO_2$ and $NH_3$ released from air stripping; high levels are attainable, which should also benefit the selectivity of $H_2S$ over $CO_2$. High gas flow rates are also typical of agricultural digesters, thus providing another opportunity for enhancement of selectivity.

In another embodiment, the method further comprises a recycling of effluent system, wherein the liquid effluent with a lower pH as a result of the biogas contact, plug flows into a subsequent vessel where the liquid is air sparged, increasing the pH to about 8-9, or event higher. This liquid can then be recycled to secondarily treat the biogas, removing additional $H_2S$ and $CO_2$.

In another embodiment, the disclosure relates to a method comprising: contacting an alkaline effluent with an input biogas to produce a treated biogas with less $H_2S$ than the input biogas and a resulting effluent with a lower pH than the alkaline effluent, and recycling the resulting effluent to increase the pH of the recycled effluent. In another embodiment, the method further comprises contacting the recycled effluent with treated biogas to produce a biogas with less $CO_2$ than the treated biogas.

In another embodiment, the disclosure relates to a method comprising: contacting an alkaline effluent with an input biogas to produce a treated biogas with less $H_2S$ than the input biogas and a resulting effluent with a lower pH than the alkaline effluent, recycling the resulting effluent to increase the pH of the recycled effluent and contacting the recycled effluent with a second input biogas to produce a second treated biogas with less $H_2S$ than the second input biogas.

In another embodiment, recycling the effluent comprises aerating the effluent. In another embodiment, recycling the effluent comprises adding an agent to increase the pH of the effluent.

Methods for Removing $H_2S$ and $CO_2$ from a Biogas

The disclosure relates to methods, systems, and apparatuses for removing $H_2S$ and $CO_2$ from biogas. In one embodiment, $H_2S$ is selectively removed over $CO_2$ from biogas in a first step and in a second step, $CO_2$ is removed from the biogas. It is possible to continue removal of $CO_2$ once the $H_2S$ has been removed. The $CO_2$ is slightly acidic and absorbs into the pretreated alkaline effluent.

To achieve this, regeneration of the spent effluent after $H_2S$ (and some $CO_2$) has been removed in the biogas purification step is required. If regeneration is possible and the pH of the effluent can be raised above about 8, $CO_2$ can continue to be removed from the biogas, further purifying the biogas of its contaminants with the goal of producing a high $CH_4$ content. This will allow farmers more choices for generating profit beyond combined heat and power. Using this approach could significantly lower the operation cost and eliminate the use and disposal of expensive chemicals (e.g. NaOH, CaO), while utilizing an alkaline byproduct, necessary in $NH_3$ stripping, and simultaneously returning the AD effluent pH back to near neutrality (pH<7.5).

In one embodiment, regenerating the effluent comprises increasing the pH of the effluent. In another embodiment, regenerating the effluent comprises aerating the effluent to increase the pH of the effluent. In yet another embodiment, regenerating the effluent comprises adding an agent to increase the pH of the effluent, including but not limited to quicklime.

In another embodiment, a method for removing contaminants from a biogas is provided comprising: (a) digesting waste material in an anaerobic digester to produce an effluent and a biogas; (b) aerating anaerobic digester effluent to produce an alkaline effluent; (c) treating the biogas from step (a) with the alkaline liquid effluent from step (b) to selectively remove $H_2S$ over $CO_2$ to produce a treated biogas composed mainly of $CH_4$ and $CO_2$ and a resulting effluent with a lower pH than the pH of the alkaline effluent; (d) regenerating the resulting effluent from step (d) to increase the pH of the resulting effluent; and (e) contacting the treated biogas of step (c) with the regenerated effluent from step (d) to remove $CO_2$ from the treated biogas. In one embodiment, regenerating the effluent comprises aerating the effluent. In yet another embodiment, regenerating the effluent comprises adding a caustic or quicklime.

In yet another embodiment, steps (d) and (e) can be repeated any number of times, including but not limited to 2, 3, 4, 5, 6, 7, 8, 9, 10, 11, 12, 13, 14, 15, and greater than 15 times.

In one embodiment, the process of steps (c), (d), and (e) can be performed in a single reactor. In another embodiment, the process of steps (c), (d), and (e) can be performed in two reactors. In yet another embodiment, the process of steps (c), (d), and (e) can be performed in three reactors.

In one embodiment, regenerating the resulting effluent from step (d) comprises contacting the resulting effluent with air. In one embodiment, regenerating the resulting effluent from step (d) comprises aerating the resulting effluent. Contact or aeration may be accomplished through the use of infusers, bubblers, fluidic Venturi reactor, sparger, gas filter, spray, tray, catalytic bubble column reactors, draft-tube type reactors or packed column reactors, and the like, as may be convenient. Where desired, two or more different biogas charging reactors (such as columns or other types of reactor configurations) may be employed, e.g., in series, such as three or more, four or more, etc.

In one embodiment, regenerating the resulting effluent from step (d) comprises aerating the effluent in any vessel that allows contact between the effluent and air.

In another embodiment, regenerating the resulting effluent from step (d) comprises aerating the effluent in a reactor using a sparger. Any sparger can be used including but is not limited to airstone, single inlet orifice, macro and micro-diffuser and a multi-site inlet orifice.

In one embodiment, the air to regenerate the effluent flows into the reactor at the bottom of the reactor through a sparger. The flow rate can be controlled by a rotameter (Cole-Parmer, IL). In one embodiment, the sparger can be an airstone sparger or a single inlet orifice or a multi-orifice. In another embodiment, the pore diameter of the sparger can be from 40 µm 500 µm. The sparger can have any desired dimensions and can be constructed out of any suitable material including but not limited to glass bonded silica.

In yet another embodiment, the reactor for regenerating the effluent can be a bubble column. The bubble column can be constructed out of any suitable material including but not limited to plastic.

In one embodiment, the reactor for regenerating the effluent can be operated batchwise with respect to the liquid and continuously with respect to the gas phase. In yet another embodiment, the reactor for regenerating the effluent can be operated continuously with respect to the liquid and gas phase. In still another embodiment, the reactor for regenerating the effluent can be operated batch-wise with respect to the liquid and gas phase.

In another embodiment, a method for removing contaminants from a biogas is provided comprising: (a) digesting waste material in an anaerobic digester to produce an effluent and a biogas; (b) aerating anaerobic digester effluent to release supersaturated gases and produce an alkaline effluent; (c) treating the biogas from step (a) with the alkaline liquid effluent from step (b) to selectively remove $H_2S$ over $CO_2$ and produce a biogas composed mainly of $CH_4$ and $CO_2$; (d) regenerating an effluent fraction produced in any step in the manure management cycle to produce a regenerated alkaline effluent; and (e) treating or contacting the biogas with the regenerated effluent from step (d) to remove $CO_2$ from the biogas. In one embodiment, regenerating the effluent fraction is achieved by aerating the effluent fraction.

In one embodiment, the effluent fraction used in step (d) can be any type of effluent including but not limited to effluent directly removed from the anaerobic digester, effluent removed from the digester and separated from large solids, effluent removed from the digester and separated from fine solids, effluent removed from the digester and separated from large and fine solids; effluent removed from the digester and aerated; effluent removed from the digester and heated; effluent removed from the digester and heated and aerated; effluent removed from the digester heated and aerated and separated from solids; effluent removed from the digester heated, aerated and used to remove $H_2S$ from a biogas, effluent removed from the digester heated, aerated, separated from solids; used to remove $H_2S$ from biogas; effluent removed from the digester heated, aerated, used to remove $H_2S$ from a biogas and regenerated to an alkaline pH; effluent removed from the digester heated, aerated, separated from solids; used to remove $H_2S$ from biogas, and regenerated to an alkaline pH; effluent removed from the digester heated, aerated, used to remove $H_2S$ from a biogas, regenerated to an alkaline pH, and used to remove $CO_2$ from a biogas; and effluent removed from the digester heated, aerated, separated from solids; used to remove $H_2S$ from biogas, regenerated to an alkaline pH and used to remove $CO_2$ from biogas.

In one embodiment, regenerating the effluent fraction is achieved by aerating the effluent fraction at an air flow rate selected from the group consisting of: 0.01-0.03 L/min, 0.03-0.06 L/min, 0.06-0.07 L/min, 0.07-0.08 L/min, 0.08-0.10 L/min, 0.10-0.12 L/min, 0.12-0.13 L/min, 0.13-0.15 L/min, 0.15-0.20 L/min, 0.20-0.25 L/min, 0.25-0.5 L/min, 0.5-0.75 L/min, 0.75-1.0 L/min, 1.0-1.5 L/min, 1.5-2.0 L/min, 2.0-2.5 L/min. 2.5-3 L/min, 3.0-3.5 L/min, 3.5-4.0 L/min. 4.0-4.5 L/min. 4.5-5.0 L/min. 5.0-5.5 L/min, 5.5-6.5 L/min, 6.5-7.5 L/min, 7.5-8.5 L/min, 8.5-9.5 L/min, 9.5-12.0 L/min, 12-15 L/min, 15-25 L/min, 25-35 L/min. 35-45 L/min, 45-55 L/min, 55-65 L/min, 65-75 L/min, 75-85 L/min, 85-95 L/min, 95-105 L/min, 105-115 L/min, and greater than 115 L/min.

In one embodiment, treating or contacting the biogas with the regenerated effluent is accomplished using a biogas flow rate selected from the group consisting of: 0.01-0.03 L/min, 0.03-0.06 L/min, 0.06-0.07 L/min, 0.07-0.08 L/min, 0.08-0.10 L/min, 0.10-0.12 L/min, 0.12-0.13 L/min, 0.13-0.15 L/min, 0.15-0.20 L/min, 0.20-0.25 L/min, 0.25-0.5 L/min, 0.5-0.75 L/min, 0.75-1.0 L/min, 1.0-1.5 L/min, 1.5-2.0 L/min, 2.0-2.5 L/min. 2.5-3 L/min. 3.0-3.5 L/min, 3.5-4.0 L/min. 4.0-4.5 L/min. 4.5-5.0 L/min. 5.0-5.5 L/min, 5.5-6.5

L/min, 6.5-7.5 L/min, 7.5-8.5 L/min, 8.5-9.5 L/min, 9.5-12.0 L/min, 12-15 L/min, 15-25 L/min, 25-35 L/min. 35-45 L/min, 45-55 L/min, 55-65 L/min, 65-75 L/min, 75-85 L/min, 85-95 L/min, 95-105 L/min, 105-115 L/min, and greater than 115 L/min.

In one embodiment, treating or contacting the biogas with the regenerated effluent is accomplished using an effluent flow rate selected from the group consisting of: 0.01-0.03 L/min, 0.03-0.06 L/min, 0.06-0.07 L/min, 0.07-0.08 L/min, 0.08-0.10 L/min, 0.10-0.12 L/min, 0.12-0.13 L/min, 0.13-0.15 L/min, 0.15-0.20 L/min, 0.20-0.25 L/min, 0.25-0.5 L/min, 0.5-0.75 L/min, 0.75-1.0 L/min, 1.0-1.5 L/min, 1.5-2.0 L/min, 2.0-2.5 L/min. 2.5-3 L/min, 3.0-3.5 L/min, 3.5-4.0 L/min. 4.0-4.5 L/min. 4.5-5.0 L/min. 5.0-5.5 L/min, 5.5-6.5 L/min, 6.5-7.5 L/min, 7.5-8.5 L/min, 8.5-9.5 L/min, 9.5-12.0 L/min, 12-15 L/min, 15-25 L/min, 25-35 L/min. 35-45 L/min, 45-55 L/min, 55-65 L/min, 65-75 L/min, 75-85 L/min, 85-95 L/min, 95-105 L/min, 105-115 L/min, and greater than 115 L/min.

In one embodiment, regenerating the effluent fraction is accomplished with an effluent volume selected from the group consisting of: 0.5-1.0 L, 1.0-1.25, 1.25-1.5, 1.5-2, 2-5 L, 5-10 L, 10-20 L, 20-40 L, 40-80 L, 80-100 L, and greater than 100 L.

In one embodiment, treating or contacting the biogas with the regenerated effluent is accomplished with an effluent volume selected from the group consisting of: 0.5-1.0 L, 1.0-1.25, 1.25-1.5, 1.5-2, 2-5 L, 5-10 L, 10-20 L, 20-40 L, 40-80 L, 80-100 L, and greater than 100 L.

The methods, systems and apparatuses disclosed herein are further described by the following number paragraphs:

1. A method for removing contaminants in a biogas comprising: (a) heating and aerating anaerobic digester effluent in an aeration reactor to produce an alkaline effluent; (b) contacting the alkaline effluent from step (a) with an input biogas in a reactor to produce a treated biogas and a resulting effluent with a lower pH as compared to the pH of the alkaline effluent; and (c) recovering the treated biogas from step (b), wherein the treated biogas has less $H_2S$ as compared to the input biogas.

2. A method for removing contaminants in a biogas comprising: (a) heating and aerating anaerobic digester effluent in an aeration reactor to produce an alkaline effluent; (b) treating an input biogas with the alkaline effluent of step (a) in a reactor to produce a treated biogas and a resulting effluent with a lower pH as compared to the pH of the alkaline effluent; and (c) recovering the treated biogas from step (b), wherein the treated biogas has less $H_2S$ as compared to the input biogas.

3. A method for removing contaminants in a biogas comprising: (a) heating and aerating anaerobic digester effluent in an aeration reactor to produce an alkaline effluent; (b) sparging or diffusing an input biogas into the alkaline effluent of step (a) in a reactor to produce a treated biogas and a resulting effluent with a lower pH as compared to the pH of the alkaline effluent; and (c) recovering the treated biogas from step (b), wherein the treated biogas has less $H_2S$ as compared to the input biogas.

4. A method for removing contaminants in a biogas comprising: (a) heating and aerating an anaerobic digester effluent in an aeration reactor to produce an alkaline effluent; (b) contacting the alkaline effluent from step (a) with an input biogas in a reactor to produce a treated biogas and a resulting effluent with a lower pH as compared to the pH of the alkaline effluent; (c) recovering the treated biogas from step (b), wherein the treated biogas has less $H_2S$ as compared to the input biogas; (d) aerating the resulting effluent of step (b) to produce a regenerated effluent with an alkaline pH; and (e) contacting the regenerated alkaline effluent of step (d) with the recovered biogas of step (c) to remove $CO_2$ in the biogas.

5. A method for removing contaminants in a biogas comprising: (a) heating and aerating an anaerobic digester effluent in an aeration reactor to produce an alkaline effluent; (b) sparging or diffusing an input biogas into the alkaline effluent from step (a) in a reactor to produce a treated biogas and a resulting effluent with a lower pH as compared to the pH of the alkaline effluent; (c) recovering the treated biogas from step (b), wherein the treated biogas has less $H_2S$ as compared to the input biogas; (d) aerating the resulting effluent of step (b) to produce a regenerated effluent with an alkaline pH; and (e) contacting the regenerated alkaline effluent of step (d) with the recovered biogas of step (c) to remove $CO_2$ in the biogas.

6. A method comprising: contacting an alkaline effluent with an input biogas to produce a treated biogas with less $H_2S$ than the input biogas and a resulting effluent with a lower pH than the alkaline effluent, and recycling the resulting effluent to increase the pH of the recycled effluent. In another embodiment, the method further comprises contacting the recycled effluent with treated biogas to produce a biogas with less $CO_2$ than the treated biogas.

7. A method comprising: contacting an alkaline effluent with an input biogas to produce a treated biogas with less $H_2S$ than the input biogas and a resulting effluent with a lower pH than the alkaline effluent, recycling the resulting effluent to increase the pH of the recycled effluent and contacting the recycled effluent with treated biogas to produce a biogas with less $CO_2$ than the treated biogas.

8. A method comprising: contacting an alkaline effluent with an input biogas to produce a treated biogas with less $H_2S$ than the input biogas and a resulting effluent with a lower pH than the alkaline effluent, recycling the resulting effluent to increase the pH of the recycled effluent and contacting the recycled effluent with a second input biogas to produce a second treated biogas with less $H_2S$ than the second input biogas.

9. A method comprising: contacting an alkaline effluent with an input biogas to produce a treated biogas with less $H_2S$ than the input biogas and a resulting effluent with a lower pH than the alkaline effluent, recycling the resulting effluent to increase the pH of the recycled effluent and contacting the recycled effluent with a second input biogas to produce a biogas with less $CO_2$ than the second input biogas.

10. A method for removing contaminants from a biogas is provided comprising: (a) digesting waste material in an anaerobic digester to produce an effluent and a biogas; (b) aerating anaerobic digester effluent to release supersaturated gases and produce an alkaline effluent; (c) treating the biogas from step (a) with the alkaline liquid effluent from step (b) to selectively remove $H_2S$ over $CO_2$ and produce a biogas composed mainly of $CH_4$ and $CO_2$; (d) regenerating an effluent fraction produced in any step in the manure management cycle to produce a regenerated alkaline effluent; and (e) treating or contacting the biogas with the regenerated effluent from step (d) to remove $CO_2$ from the biogas 11. The method of any of paragraphs 1-10, further comprising prior to step (a), digesting waste material to produce an effluent and a biogas.

12. The method of any of paragraphs 1-11, wherein heating and aerating the anaerobic digester effluent releases supersaturated gases and produces an alkaline effluent.

13. The method of any of paragraphs 1-12, further comprising adding an agent in step (a) to help increase the pH of the effluent and produce an alkaline effluent.

14. The method of any of paragraphs 1-13, wherein the agent is quicklime or a similar agent.

15. The method of any of paragraphs 1-14, wherein the contacting, treating, sparging or diffusing between the effluent and biogas occurs in a bubble column.

16. The method of any of paragraphs 1-15, wherein the biogas and effluent are contacted, treated, sparged or diffused in by infusers, bubblers, fluidic Venturi reactor, sparger, gas filter, spray, tray, catalytic bubble column reactors, draft-tube type reactors or packed column reactors.

17. The method of any of paragraphs 1-16, wherein contacting comprises direct contacting protocols, e.g., bubbling the gas through the volume of effluent, concurrent contacting means, i.e., contact between unidirectionally flowing gaseous and liquid phase streams, countercurrent means, i.e., contact between oppositely flowing gaseous and liquid phase streams, and the like.

18. The method of any of paragraphs 1-17, wherein the gaseous stream contacts the effluent source vertically, horizontally, or at some other angle.

19. The method of any of paragraphs 1-18, wherein the biogas may be contacted with the effluent source from one or more of the following positions: below, above, or at the surface level.

20. The method of any of paragraphs 1-19, wherein $H_2S$ is selectively removed over $CO_2$.

21. The method of any of paragraphs 1-20, wherein the biogas has a gas velocity selected from the group consisting of: 0.0015-0.0025 $m \cdot s^{-1}$, 0.0025-0.0037 $m \cdot s^{-1}$, 0.0037-0.0047 $m \cdot s^{-1}$, 0.0047-0.0057 $m \cdot s^{-1}$, 0.0057-0.0067 $m \cdot s^{-1}$, 0.0067-0.0077 $m \cdot s^{-1}$, 0.0077-0.0087 $m \cdot s^{-1}$, 0.0087-0.0097 $m \cdot s^{-1}$, 0.0097-0.0100 $m \cdot s^{-1}$, 0.01-0.02 $m \cdot s^{-1}$, 0.02-0.04 $m \cdot s^{-1}$, 0.04-0.06 $m \cdot s^{-1}$, 0.06-0.08 $m \cdot s^{-1}$, 0.08-0.1 $m \cdot s^{-1}$, 0.1-0.2 $m \cdot s^{-1}$, 0.2-0.4 $m \cdot s^{-1}$, 0.4-0.6 $m \cdot s^{-1}$, 0.6-0.8 $m \cdot s^{-1}$, 0.8-1.0 $m \cdot s^{-1}$, 1-2 $m \cdot s^{-1}$, 2-4 $m \cdot s^{-1}$, 4-6 $m \cdot s^{-1}$, 6-8 $m \cdot s^{-1}$, 8-10 $m \cdot s^{-1}$ and greater than 10 $m \cdot s^{-1}$.

22. The method of any of paragraphs 1-21, wherein aerating the anaerobic digester effluent is accomplished using micro-aerators that aerate the effluent at a rate from 5 gallons/cfm to 25 gallons/cfm.

23. The method of any of paragraphs 1-22, wherein contacting the alkaline effluent with an input biogas comprises using an alkaline effluent with a pH from about 9.0 to about 12.0.

24. The method of any of paragraphs 1-23, wherein the bubble column has a churn-turbulent flow regime.

25. The method of any of paragraphs 1-24, wherein contacting the alkaline effluent with an input biogas comprises a gas:liquid ratio selected from the group consisting of: 20:1, 21:1, 22:1, 23:1, 24:1, 25:1, 26:1, 27:1, 28:1, 29:1, and 30:1.

26. The method of any of paragraphs 1-25, wherein contacting the alkaline effluent with an input biogas comprises a gas:liquid ratio of 21-25:1.

27. The method of any of paragraphs 1-26, wherein regenerating the effluent comprises aerating the effluent.

28. The method of any of paragraphs 1-27, wherein regenerating the effluent comprises adding a caustic or quicklime.

The invention is now described with reference to the following Examples. These Examples are provided for the purpose of illustration only and the invention should in no way be construed as being limited to these Examples, but rather should be construed to encompass any and all variations that become evident as a result of the teaching provided herein. All references including but not limited to U.S. patents, allowed U.S. patent applications, or published U.S. patent applications are incorporated within this specification by reference in their entirety.

EXAMPLES

Example 1

The aim of these experiments was to determine the selectivity of $H_2S$ over $CO_2$ from biogas as well as the $H_2S$ removal efficiency of an alkaline effluent, produced as a by-product of anaerobic digestion and nutrient recovery, as a function of sparger design, effluent height in the reactor and superficial gas velocity.

Materials and Methods

A. Nutrient Recovery Process

Anaerobically digested dairy effluent was obtained from a dairy processing manure from 5,000 cows via a mesophilic complete mixed plug flow digester (DVO Inc., Chilton Wis.), with a hydraulic retention time of around 21 days. Fiber was separated from the effluent with a slope screen, 0.5 cm mesh (US Farms, Tulene, Calif., USA). The effluent was stored in plastic buckets at 15-20° C. in a temperature controlled room.

The pretreatment of the effluent, depicting a $NH_3$ stripping process (Zhao et al., 2012), involved extended physical aeration (~46 L·min-1) of post AD/fiber-separated dairy manure at 35° C. for 24 hours with the inclusion of 5 ml of Y-30 emulsion antifoam for foam control (Sigma-Aldrich, MO, USA). After aeration, the effluent was left for 24 hours to settle out solids. The supernatant, now with a pH of 9.81±0.02, was used that day as an alkaline absorbent during the experimental trials or stored in freezer for later use.

B. Operating Conditions

Figure 6:
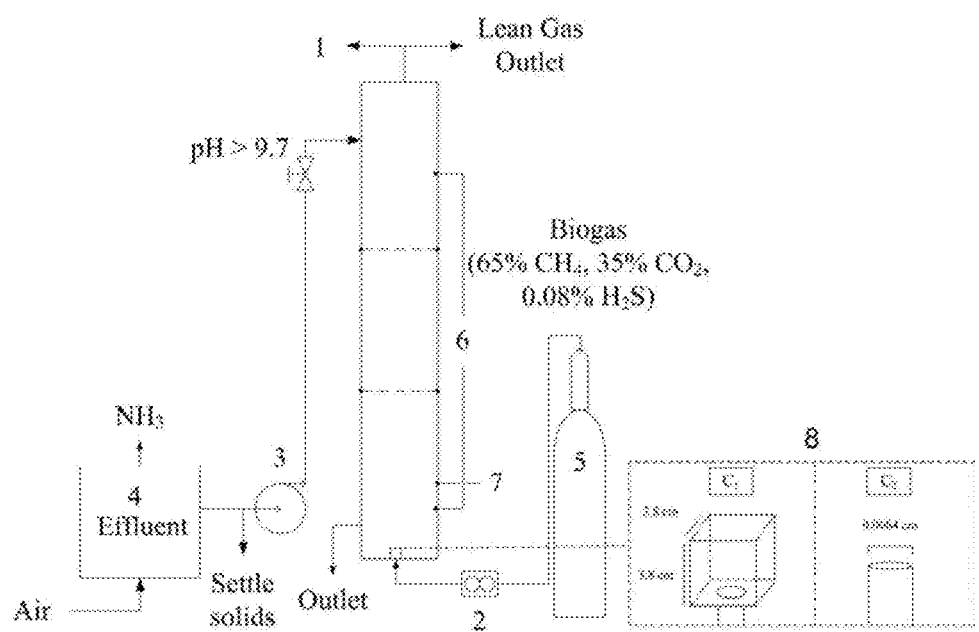
FIG. 6 is a schematic of the nutrient recovery process and bubble column reactor. (1) gas sampling port analyzed by GC; (2) rotameter for flow rate control into reactor; (3) peristaltic pump for inserting pretreated effluent into reactor; (4) $NH_3$ stripping process; (5) synthetic biogas; (6) online pH probes that connect to computer; (7) liquid sampling port; (8) types of the spargers used ($C_1$ and $C_2$ represent the airstone and inlet orifice, respectively) (not to scale)

FIG. 6 depicts the bubble column reactor that was constructed for lab-scale testing. In addition, the nutrient recovery process (4) is included in the schematic because it produces an alkaline effluent, which can be used as an absorbent of $H_2S$ and $CO_2$ from biogas. The bubble column was constructed out of plastic with a diameter of 0.072 m. The height of the bubble column ranged between 0.21 to 0.56 m, depending on the experimental run. The reactor height was altered by dividing the column into three sections fitted with rubber couplings that could be added or subtracted depending on the height required. A gas sampling port (1) is located at the top of the bubble column. A liquid sampling port (7) is located toward the bottom of the bubble column.

Biogas containing typical concentrations of $CH_4$, $CO_2$ and $H_2S$ produced at agriculture digesters was stored in a gas cylinder for use during experiments (5) (Ideal Specialty Gas and Analytical Services, Houston, Tex.). The pretreated effluent, now at alkaline conditions, was pumped into the top of the bubble column reactor by a peristaltic pump (3) (Cole Parmer, Vernon Hills, Ill.) to the appropriate height required.

Once the effluent was completely pumped into the bubble column, the inlet was shut off to ensure no biogas or liquid would escape during the experiment. The biogas flowed into the reactor at the bottom of the bubble column through either an inlet orifice or airstone sparger and was controlled by a rotameter (2) (Cole-Parmer). Online pH probes (6) were used to measure the pH conditions in the bubble column.

The types of spargers used are shown in (8). The inlet orifice had a diameter of 0.0064 cm, while the airstone had a pore diameter of 140 μm. The airstone sparger dimensions were 3.8×3.8 cm and constructed out of glass bonded silica (Aquatic Ecosystems, Apopka, Fla.) (Table 1).

TABLE 1

Operating Conditions

| Name | Description | Value and Type |
|---|---|---|
| Sparger | Inner Diameter | 0.076 m |
| | Type | airstone, single inlet orifice |
| Operating Conditions | Maximum Pore Size/Diameter | 140 μm[1], 0.64 cm |
| | Temperature | 16 ± 2° C. |
| | Pressure | 1 atm |
| | Superficial Gas Velocity | 0.0022 to 0.012 m·s$^{-1}$ |
| | Effluent Height | 0.066 to 0.48 m |
| | pH (initial) | 9.8 ± 0.01 |

The bubble column reactor was operated batch-wise with respect to the liquid phase and continuously with respect to the gas phase in the height and velocity experiments. In countercurrent experiment, the gas and liquid were operated in continuous operation. As the gas was fed into the bubble column, a stop watch was used to track the time. A port was constructed at the top of the reactor to take samples of the biogas (1). A 60 ml syringe was used to extract biogas periodically and stored in Gas samples were collected from ports located at the top and bottom of the column and stored in 12 ml borosilicate vials (Labco Limited, Wycombe, Buckinghamshire, England) every 15 seconds to 5 minutes depending on experimental run and analyzed with a Varian gas chromatograph (GC) (Santa Clara, Calif., USA), which is equipped with a thermal conductivity probe using method described in Wen at al. (2007). $CH_4$, $CO_2$, and $H_2S$ were quantified based on a calibration curve. The inability to exactly pinpoint the exact time breakthrough of $H_2S$ from the liquid back to the gas occurred throughout many of the tests and equipment noise reduced the accuracy of $H_2S$ detection in the gas to ≥30 ppm. Therefore, to have greater accuracy on determining the change each experiment had on the G/L ratio, a target of 95% removal was used as a comparative tool. On-line pH of the effluent was analyzed with an OM-CP-PH101 pH and temperature data logger connected to a PHE-4200 pH probe (6) (Omega Engineering, Stamford, Conn., USA).

Results

The selectivity of $H_2S$ over $CO_2$ was performed by altering the sparger configuration (single inlet orifice vs. an airstone sparger) at a superficial gas velocity of 0.0037 m·s$^{-1}$ and effluent height of 0.27 m. The superficial gas velocity was calculated by taking the volumetric flow rate of the gas divided by the cross-sectional area of the bubble column. In addition, experiments were conducted by varying the effluent height in the bubble column reactor while holding the superficial gas velocity constant at 0.0073 m·s$^{-1}$.

Figure 7A:
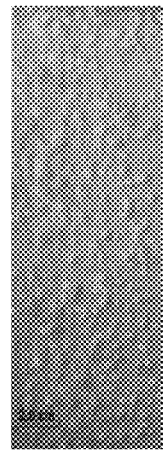
FIG. 7A is a photograph showing a bubbly flow regime, which was dominant when utilizing the airstone sparger.
Figure 7B:
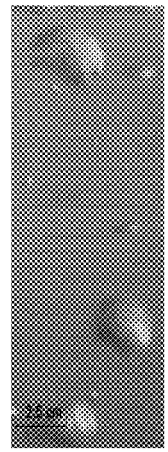
FIG. 7B is a photograph showing a churn-turbulent regime, which was dominant when utilizing the inlet orifice sparger.

An airstone and single inlet orifice sparger were tested for their capability of selectively removing $H_2S$ over $CO_2$. From the photographs taken during the selectivity study, two distinctly different flow regimes took place; a bubbly regime was dominant when utilizing the airstone sparger (FIG. 7A) and a churn-turbulent regime was dominant when utilizing the inlet orifice sparger (FIG. 7B).

Figure 8:
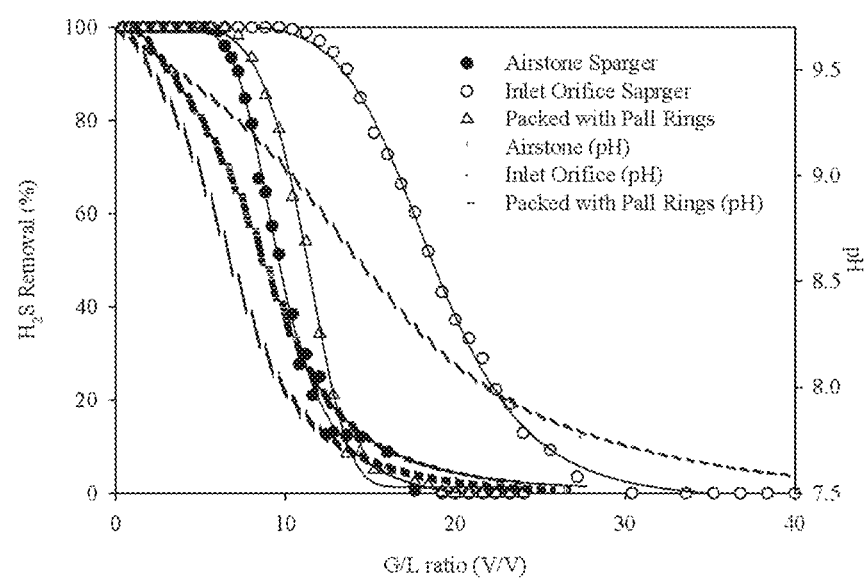
FIG. 8 is a line graph showing $H_2S$ removal efficiency using an inlet orifice, a bubble column and airstone sparger.

As a result, the sparger choice had a significant effect on the G/L ratio at 95% $H_2S$ removal (FIG. 8). The $H_2S$ removal efficiency was originally as a function of time and converted to a function of the G/L ratio by multiplying the volumetric flow rate by the time and dividing that by the volume of effluent inside the reactor at 16° C. and 1 atm. Converting the $H_2S$ removal efficiency as a function of time to a function of the G/L ratio allowed for a better comparison of the difference in removal of $H_2S$ using the two spargers.

Figure 9:
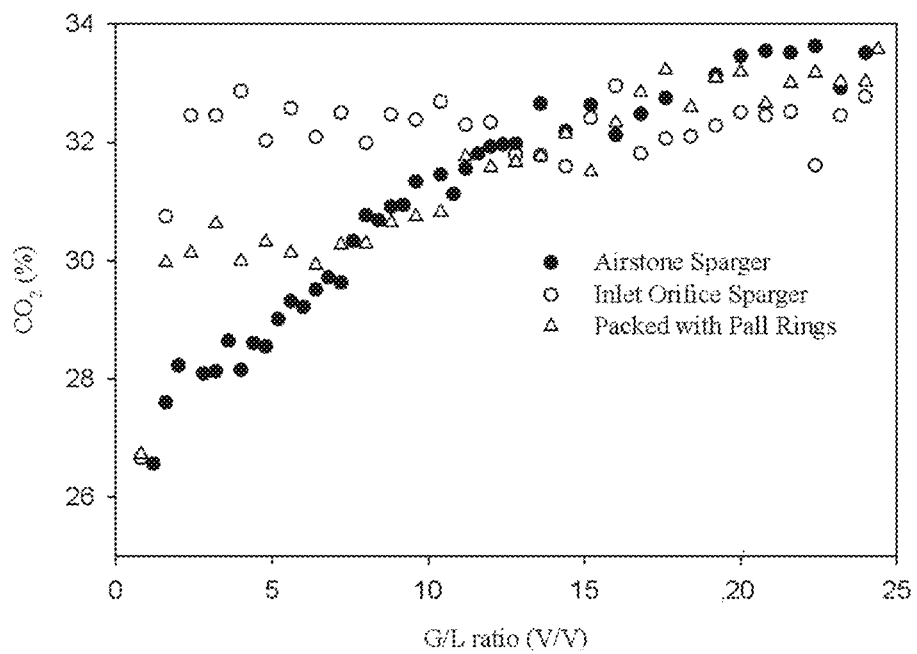
FIG. 9 is a graph showing percent $CO_2$ when utilizing an airstone sparger, inlet orifice sparger and bubble column packed with pall rings as a function of the G/L ratio.

The G/L ratio at 95% $H_2S$ removal increased by roughly 50% when using the inlet orifice sparger compared to the airstone sparger, simply by changing the way the bubbles emit from the sparger. The airstone sparger promoted the formation of a relatively uniform dense population of small bubbles, which increased the gas holdup compared to the inlet orifice sparger To gain better insight into the main reason why the $H_2S$ removal efficiency dropped so significantly, a comparison between the two sparger configurations on $CO_2$ removal was measured. FIG. 9 illustrates that there was a significant increase in $CO_2$ absorption into the effluent when utilizing the airstone sparger since the amount of $CO_2$ leaving the reactor reduced to about 27% at the beginning of the experiment and over time steadily increased to its final concentration of around 33%. This reduced the selectivity of $H_2S$ because of an increase in the production of $H_3O^+$ during carbonate ($HCO_3^-$) and bicarbonate ($CO_3^{2-}$) formation which subsequently decreased the pH at a quicker rate than when using the inlet orifice sparger. Any increase in $CO_2$ absorption will impact the reduction rate of the effluent pH and effectively decrease $H_2S$ absorption because the strong enhancement effect for the disassociation of $H_2S$ occurs only at pH greater than 9.

To justify that altering the interfacial area was the main reason CO2 absorption reduced when using the inlet orifice sparger, 25.4-mm plastic pall rings with a surface area of 210 $m^2 \cdot m^3$ (Jaeger Products, Houston, Tex.) were randomly placed in the bubble column to artificially increase the gas liquid surface area. The $CO_2$ concentration profile shown in FIG. 9 includes the pall ring experiment and similar trends can be seen; much less $CO_2$ came out of the reactor when compared with the inlet orifice sparger, while being slightly more selective for $H_2S$ than the airstone sparger.

Figure 10:
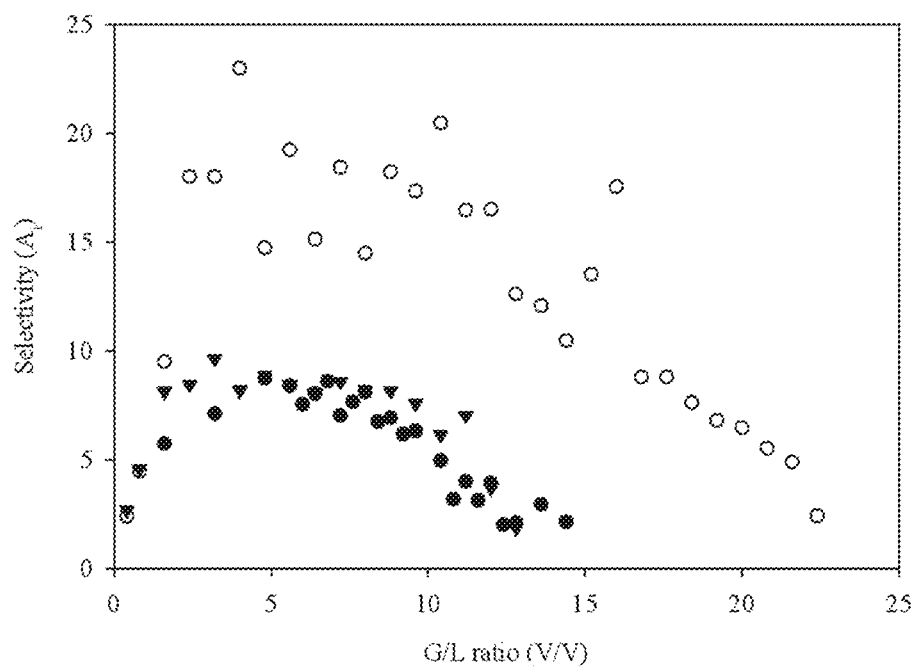
FIG. 10 is a graph showing the selectivity factor for the two sparger configurations as well as the bubble column packed with pall rings as a function of the G/L ratio.

The selectivity factor for $H_2S$ over $CO_2$ was calculated from the start of the absorption experiment until complete saturation of effluent was achieved for both sparger configurations. A distinct difference was found when using the airstone and the bubble column packed with plastic pall rings compared to the inlet orifice (FIG. 10). The selectivity factor increased significantly after a G/L ratio of 2:1 and a large difference was achieved with the inlet orifice up until complete saturation of the effluent at around 23:1. The selectivity factor was similar for both the airstone sparger and packed bubble column, with slightly more selectivity achieved using the packing material.

From this study, selectivity was achieved using a bubble column by altering the way the bubbles are injected into the alkaline effluent. Contrary to most bubble column applications, for example fermentation, where high mass transfer of one species is critical for enhanced growth, an increase in the interfacial area is not beneficial for selectively targeting one species over another. In comparison, a bubble column may not allow for as high a degree of selectivity as a packed bed. But, since there is no need for regeneration of the absorbent, due to its continual production from the AD and nutrient recovery process, high selectivity using a complex reactor should not outweigh the cost benefits to using a bubble column.

Example 2

This experiment was designed to investigate the effects the height of the bubble column would have on $H_2S$ removal.

The G/L ratio at 95% $H_2S$ removal was further enhanced by decreasing the effluent height in the reactor. The effluent heights tested were 0.072, 0.13, 0.27, 0.42, and 0.48 m. The superficial gas velocity was held constant at 0.0073 m·s$^{-1}$. Since a significant increase in the selectivity resulted from the use of the inlet orifice in the previous sparger experiment, the same diameter inlet orifice was used as the gas injector in the remainder of experiments.

Figure 11:
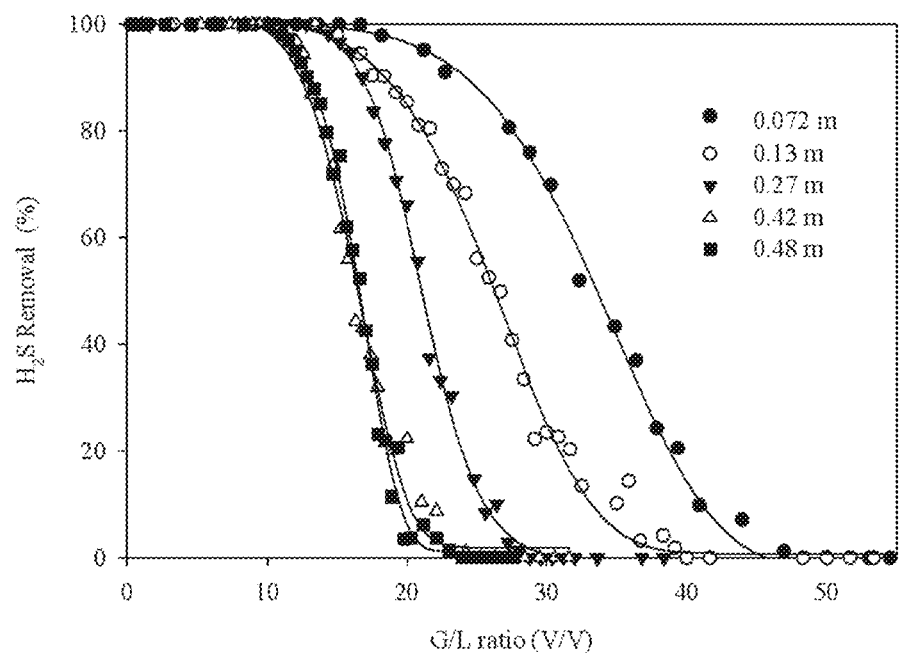
FIG. 11 is line graph showing the effect that effluent height has on the $H_2S$ removal efficiency and G/L ratio.

FIG. 11 graphically illustrates how the effluent height affects the H$_2$S removal efficiency as function of G/L ratio. At a height of 0.072 m the G/L ratio achieved roughly 21:1, while at an effluent height of 0.48 m the G/L ratio dropped to roughly 12:1. An increase of 43% on the G/L ratio, at a removal efficiency of 95%, resulted by decreasing the effluent height.

Example 3

This experiment was designed to investigate the effects gas velocity would have on H$_2$S removal.

The G/L ratio at 95% H$_2$S removal was also enhanced by increasing the superficial gas velocity. The superficial gas velocity was altered while the effluent height was kept constant at 0.27 m. The superficial gas velocities tested were 0.0022, 0.0037, 0.0073, 0.011, 0.015 m·s$^{-1}$.

Figure 12:
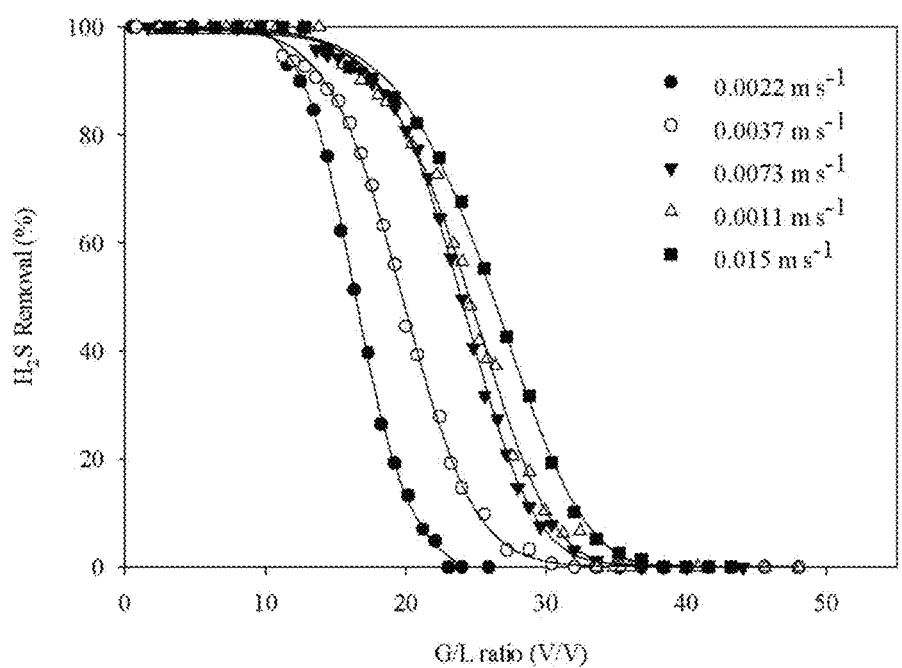
FIG. 12 is line graph showing the effect that superficial gas velocity has on the $H_2S$ removal efficiency and G/L ratio.

FIG. 12 graphically illustrates how the superficial gas velocity affects the H$_2$S removal efficiency as function of G/L ratio. An increase in the G/L ratio at 95% H$_2$S removal resulted from 0.002 to 0.015 m·s−1. The G/L ratio at 95% removal increased from around 12:1 to 17:1, which is equivalent to a 29% increase in the amount of biogas that can be purified per effluent.

Example 4

Since the previous experiments were conducted in a semi-continuous mode of operation, countercurrent operation was investigated. Countercurrent operation was then tested at an effluent height of 0.072 m and gas flow rate of 2.0 L·min$^{-1}$.

Figure 13:
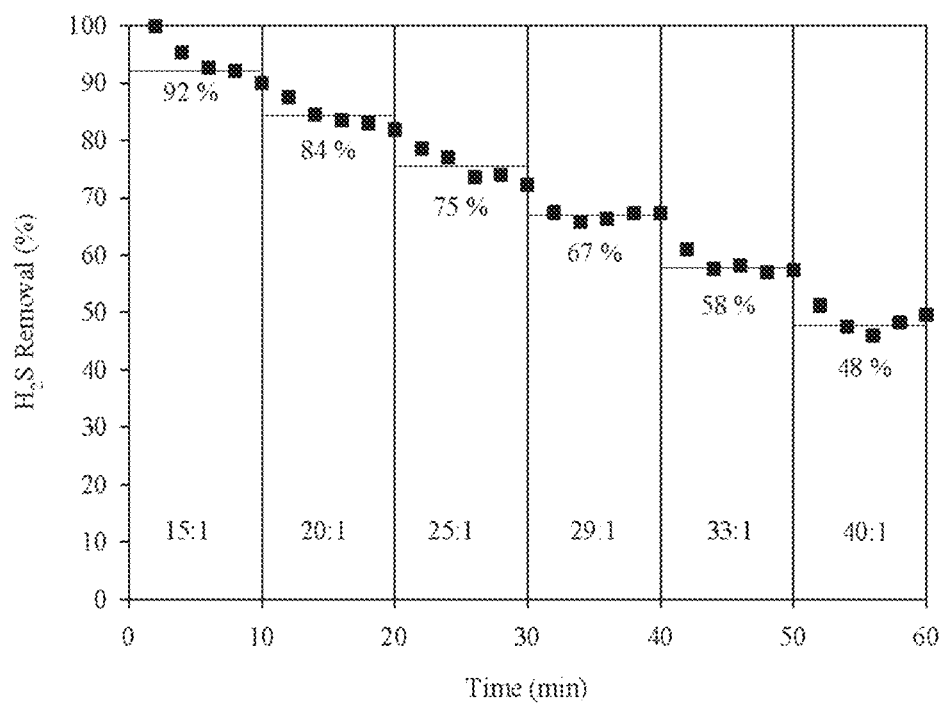
FIG. 13 is a graph showing the effect that altering liquid flow rate has on the $H_2S$ removal efficiency and G/L ratio.

The following liquid flow rates tested were 0.13, 0.10, 0.08, 0.07, 0.06 and 0.13 L·min$^{-1}$. This provided equivalent G/L (v/v) ratios of 15, 20, 25, 29, 33, and 40:1. FIG. 13 illustrates the countercurrent operation as a function of time. At a G/L ratio of 15:1, 92% H$_2$S removal was achieved, but as the G/L ratio began to increase due to a decrease in the liquid flow rate, the H$_2$S removal efficiency dropped. Unfortunately, a G/L ratio of 21:1 could not be tested due to a lack of precision with the peristaltic pump. Although, at a G/L ratio of 20:1, the removal efficiency was around 84%, which is lower than what was determined in the semi-continuous experiments.

This G/L ratio was slightly lower than the low-end target of an agricultural digester (21:1), but does give insight into the level of efficiency that can be achieved. At the higher target G/L ratio of typical agricultural digesters (25:1), the removal efficiency was reduced to around 75%. The removal efficiency never decreases below 45%, even when the G/L ratio was 40:1.

By manipulating the bubbles, decreasing the effluent height, and increasing the superficial gas velocity, the selective removal of H$_2$S over CO$_2$ from biogas was increased. This is the first time the selective removal of H$_2$S over CO$_2$ has been investigated in a bubble column reactor using the byproduct of the AD and NH$_3$ stripping process.

Since relatively high H$_2$S removal efficiency (84%) was achieved in countercurrent operation using this simple and low cost apparatus at G/L ratios typically produced at agriculture digesters (20:1), this technique could be adopted to reduce the concentration of H$_2$S prior to combustion in an internal combustion engine or further upgrading to meet pipeline quality or biomethane standards.

These experiments demonstrate that it is possible to selectively remove H$_2$S over CO$_2$ in a bubble column at a high removal efficiency and biogas-to-effluent ratios close to the ratios produced at agricultural digesters (21-25:1). H$_2$S was solely targeted in these examples due to its detrimental effects to the environmental (SO$_x$ emissions) and health effects. In addition, H$_2$S is detrimental to almost every upgrading process because of its corrosive capability. Furthermore, it is detrimental to internal combustion engines because upon combustion converts to sulfuric acid. High removal efficiency for H$_2$S was achieved in countercurrent operation (>94%) at biogas-to-effluent ratios slightly lower (15:1) than the target introduced earlier.

Example 5

Introduction

As discussed and demonstrated above, contacting the effluent with biogas removes H$_2$S and some CO$_2$. This experiment demonstrates that sequential purification and regeneration steps can be used to remove additional CO$_2$ in the biogas. It is possible to continue removal of CO$_2$ once the H$_2$S has been removed. The CO$_2$ is slightly acidic and absorbs into the pretreated alkaline effluent.

To achieve this, regeneration of the spent effluent after H$_2$S (and some CO$_2$) has been removed in the biogas purification step is required. If regeneration is possible and the pH of the effluent can be raised above about 8, CO$_2$ can continue to be removed from the biogas, further purifying the biogas of its contaminants with the goal of producing a high CH$_4$ content. This will allow farmers more choices for generating profit beyond combined heat and power. Using this approach could significantly lower the operation cost and eliminate the use and disposal of expensive chemicals (e.g. NaOH, CaO), while utilizing an alkaline byproduct, necessary in NH$_3$ stripping, and simultaneously returning the AD effluent pH back to near neutrality (pH<7.5).

Figure 14:
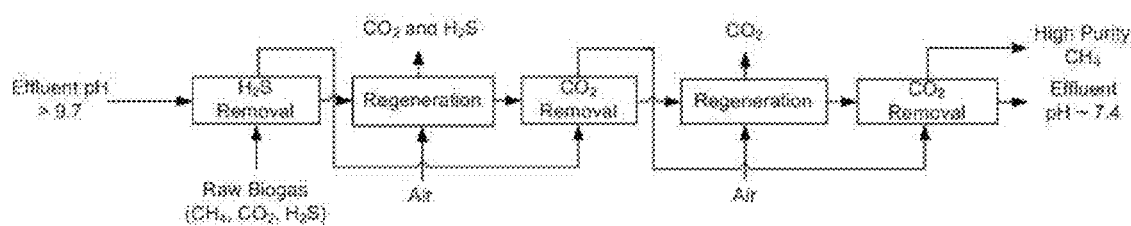
FIG. 14 is schematic of the sequential purification of both $H_2S$ and $CO_2$ from biogas. After removing $H_2S$ and some $CO_2$, the effluent is regenerated by aerating the effluent. Once a suitable alkaline pH has been achieved, the aerated effluent is used to remove residual $CO_2$ in the biogas. This process of regenerating the effluent and removing $CO_2$ can be repeated as many times as desired.

FIG. 14 depicts the biogas purification and regeneration processes for the stepwise removal of both H$_2$S and CO$_2$ from the biogas. H$_2$S is removed in the first step since it has a lower initial concentration in the biogas than CO$_2$ and thus is easier to completely remove. The selective removal of H$_2$S over CO$_2$ is discussed throughout the specification and in Examples 1-4.

The subsequent step is a regeneration step to raise the pH back to above 9 by knocking out both H$_2$S and CO$_2$ from the effluent. This step is achieved by re-aerating the effluent. After a suitable pH of the aerated effluent, which can range from 8 to 12, has been achieved, the effluent is sent into another reactor where CO$_2$ can be removed from the biogas that has already been purified of H$_2$S.

This process can be repeated as many times as needed to completely remove CO$_2$ from the biogas, which will result in high purity of CH$_4$ that can be used in a variety of ways including electricity, pipeline quality gas, or as a vehicle fuel.

Conditions

Figure 15:
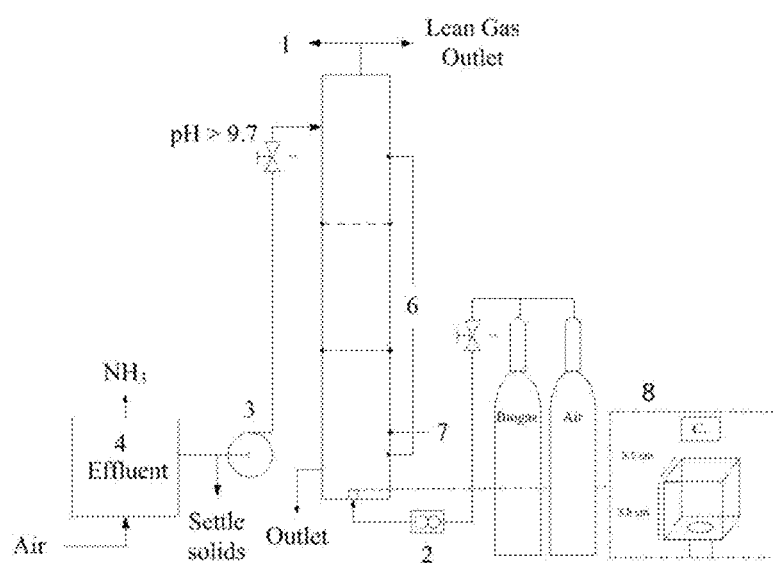
FIG. 15 is a schematic of the bubble column reactor used for the purification of the biogas and the regeneration of the effluent.

FIG. 15 depicts the bubble column reactor that was constructed for lab-scale testing. In addition, the NH$_3$ stripping process (4) is included in the schematic because it allows for the effluent, coming off the digester, to be used as an absorbent of H$_2$S and CO$_2$ from biogas. The bubble column was constructed out of plastic with a diameter of 0.072 m. One of ordinary skill in the art will understand that the bubble column can have the desired dimensions to accommodate the volume of effluent.

Biogas containing typical concentrations of $CH_4$, $CO_2$ and $H_2S$ produced at agriculture digesters was stored in a gas cylinder for use during experiments (5) (Ideal Specialty Gas and Analytical Services, Houston, Tex.). The pretreated effluent, now at alkaline conditions, was pumped into the top of the bubble column reactor by a peristaltic pump (Cole Parmer, Vernon Hills, Ill.) to the appropriate volume (1.25 L). Once the effluent was completely pumped into the bubble column, the inlet was shut off to ensure no biogas or liquid would escape.

The biogas and air flowed into the reactor at the bottom of the bubble column through an airstone sparger and was controlled by a rotameter (Cole-Parmer, IL) (2). The airstone had a pore diameter of 140 μm. The airstone sparger dimensions were 3.8×3.8 cm and constructed out of glass bonded silica (Aquatic Ecosystems, Apopka, Fla.). The bubble column was operated batchwise with respect to the liquid and continuously with respect to the gas phase.

As shown in FIG. 15, a separate tank of air was included and connected to the same tube as the biogas tank. This air tank was used to regenerate the effluent once the effluent had become completely saturated in $H_2S$ and $CO_2$. A three way valve was incorporated to be able to shut off the biogas from entering the bubble column and allow air to enter and vice versa.

An experiment was designed to confirm that it was possible to regenerate the effluent by re-aerating the effluent after the initial purification step. This test was performed at 16° C. because it has been shown by many researchers that $H_2S$ selectivity is enhanced at a lower temperature. The biogas and air flow rates were 1.0 L/min and the pretreated effluent volume was 1.25 L. The initial pH of the effluent was around 9.8.

Results

Figure 16:
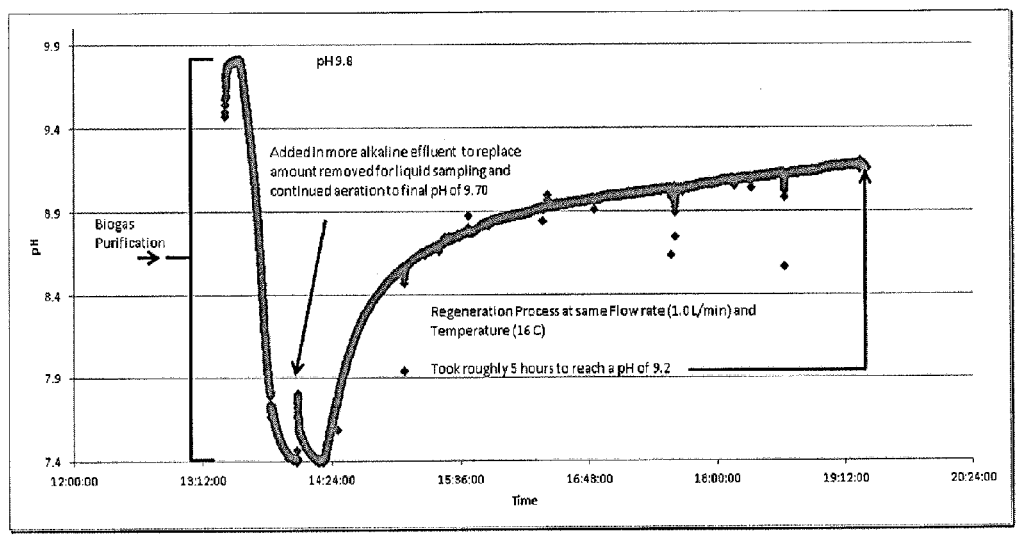
FIG. 16 is a graph depicting the affect the two-step biogas purification and regeneration process had on effluent pH.

FIG. 16 shows the affect the biogas purification process and subsequent regeneration process had on the pH of the effluent as a function of time. The pH probe needs to reach a steady state, which explains why the beginning pH increases from around 9.5 to 9.8. After a steady pH has been obtained, the biogas was injected into the bubble column through the airstone sparger. A fast drop of pH resulted from the absorption of $H_2S$ and $CO_2$ in the purification step. This process takes about 30 minutes to complete before a steady pH of around 7.4 is achieved.

Liquid samples were taken to test the total inorganic carbon in the effluent. To compensate for the volume removed, fresh pretreated effluent was added into the bubble column to reach the same liquid volume used. This resulted in a slight increase in pH after a pH of 7.4 was reached. Thereafter, biogas was injected into the effluent until the pH dropped back to 7.4.

Once a pH of 7.4 was reached, the biogas was shut off and the air was injected into the bubble column at 1.0 L/min through the airstone sparger to see if $CO_2$ and $H_2S$ could be knocked out of the effluent and raise the pH of the effluent for continued use as an absorbent of $CO_2$. As shown in FIG. 16, the pH begins to increase and after about 5 hours of aeration, the pH is about 9.2. This step takes about 10 times longer than the purification process (5 hours).

Of note, if the $H_2S$ is completely removed in the first step, a high pH does not need to be achieved in the regeneration step since $CO_2$ will absorb at a lower pH. As can be seen in FIG. 16, the pH increases rather rapidly in the beginning of the regeneration step and thereafter begins to slow down. Temperature of the effluent is important factor since if the temperature is higher the solubility of the gases decrease and should benefit the removal of $CO_2$ and $H_2S$ during the regeneration step.

Figure 17:
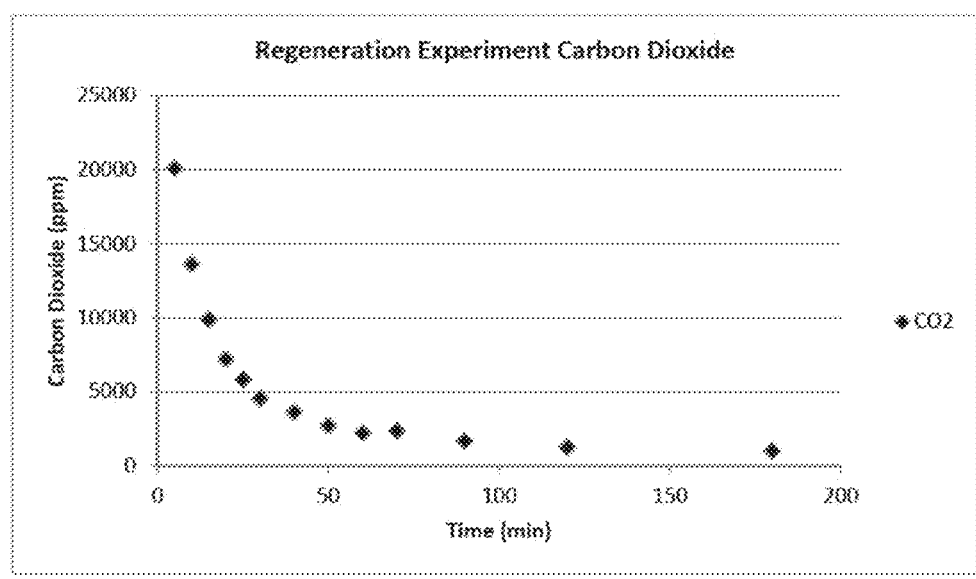
FIG. 17 is a graph depicting concentration of $CO_2$ over time during the regeneration experiment.

The gas coming out of the reactor during the regeneration process was tested periodically with Gas Chromatography to see how much $CH_4$, $CO_2$ and $H_2S$ is knocked out of the effluent once it has become saturated during the biogas purification step. FIG. 17 shows a concentration profile of $CO_2$ over time during the regeneration process. Initially, a significant quantity of $CO_2$ (0.05% of the concentration in the biogas) is kicked out of the effluent and thereafter begins to decrease in concentration.

Figure 18:
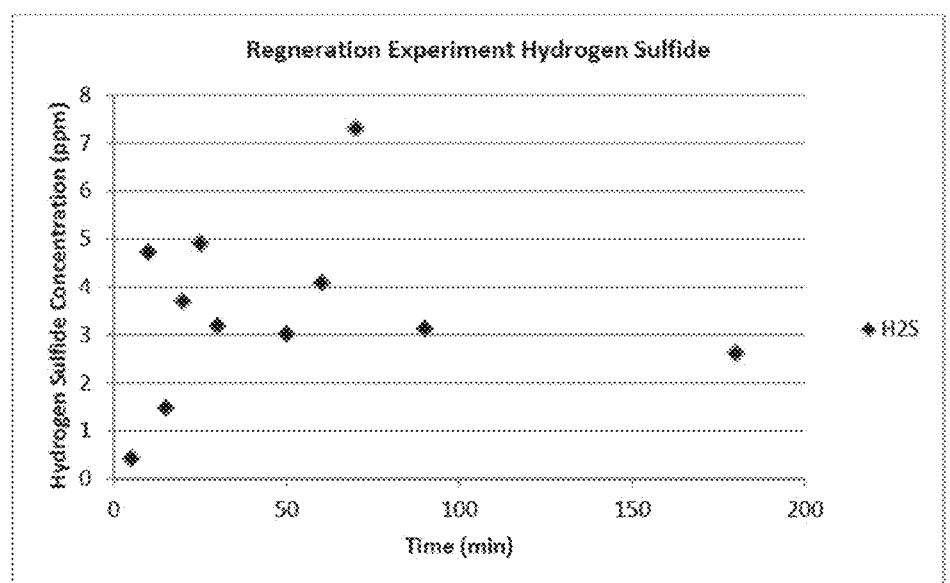
FIG. 18 is a graph depicting concentration of $H_2S$ over time during the regeneration experiment.

Even though it decreases over time $CO_2$ is knocked out throughout the regeneration process. Since $CO_2$ is slightly acidic, any amount that is knocked out of the effluent will affect the pH of the effluent, which can be seen in FIG. 16. A similar trend is found with the $H_2S$ concentration profile (FIG. 18).

The trend is not as consistent as that for $CO_2$, which could be due to a lack of precision on the GC or a variety of other reasons. Nonetheless, FIG. 18 shows over time that $H_2S$ is being kicked out as well, which effectively increases the pH of the effluent. The highest concentration knocked out of the effluent was around 7 ppm (0.008% the initial concentration in the biogas).

Figure 19:
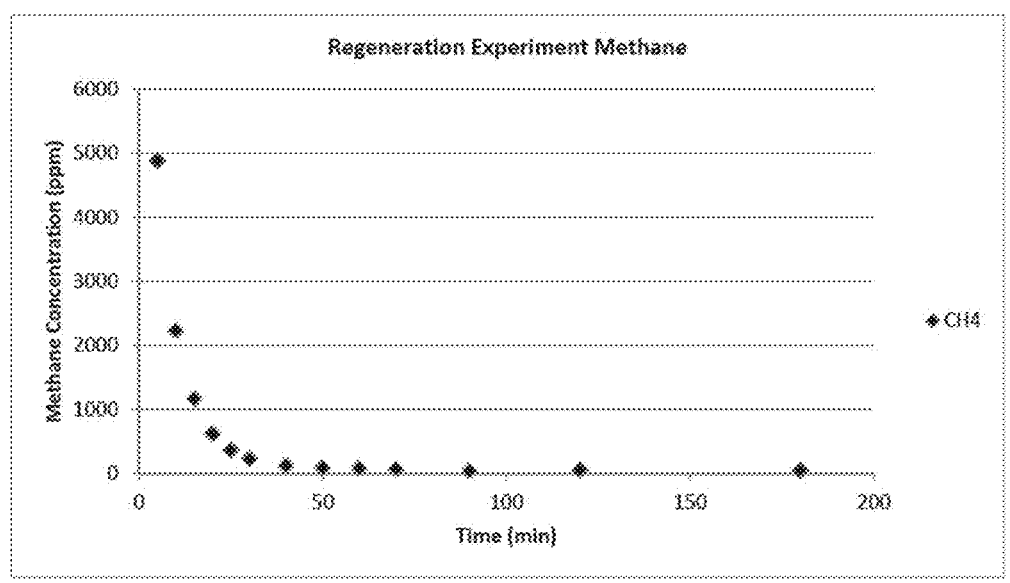
FIG. 19 is a graph depicting the concentration of methane against time during regeneration experiment.

$CH_4$ is not as soluble as $CO_2$ and $H_2S$ in liquid and thus, should not absorb into the effluent. FIG. 19 shows the amount of $CH_4$ that is knocked out of the effluent during the regeneration experiment over time. This $CH_4$ could be from the purification step (highly plausible) or supersaturated $CH_4$ from the anaerobic digestion process (not as plausible). Both could contribute but if it is supersaturated $CH_4$ from the AD process it should have already been knocked out during the $NH_3$ stripping process. Either way, the amount is rather low (0.008% at t=1 min when compared with the initial concentration in the biogas) and after around 50 minutes drops to around 0 ppm.

Example 6

A process of purification, regeneration of effluent, purification of biogas, regeneration of effluent, purification of biogas, and regeneration of effluent could provide a clean biogas with numerous utilities. The process of purification and regeneration can be repeated as many times as desired. The process of purification and regeneration can be repeated until a desired purity of biogas is achieved.

In this example, a higher temperature (35° C.) was used to see if the regeneration step could be shortened over time. A heat exchanger could be used before the initial purification process to lower the temperature (more selectivity for $H_2S$ removal) of the effluent coming off the nutrient recovery process and a second heat exchanger could be used to heat up the effluent coming out of the purification process (faster regeneration). The operating conditions for this experiment were the following: biogas flow rate: 0.5 L/min, air flow rate: 2.5 L/min, effluent volume: 1.25 L. Included in this test was the nutrient recovery process of fresh AD effluent, post-fiber separation.

Figure 20:
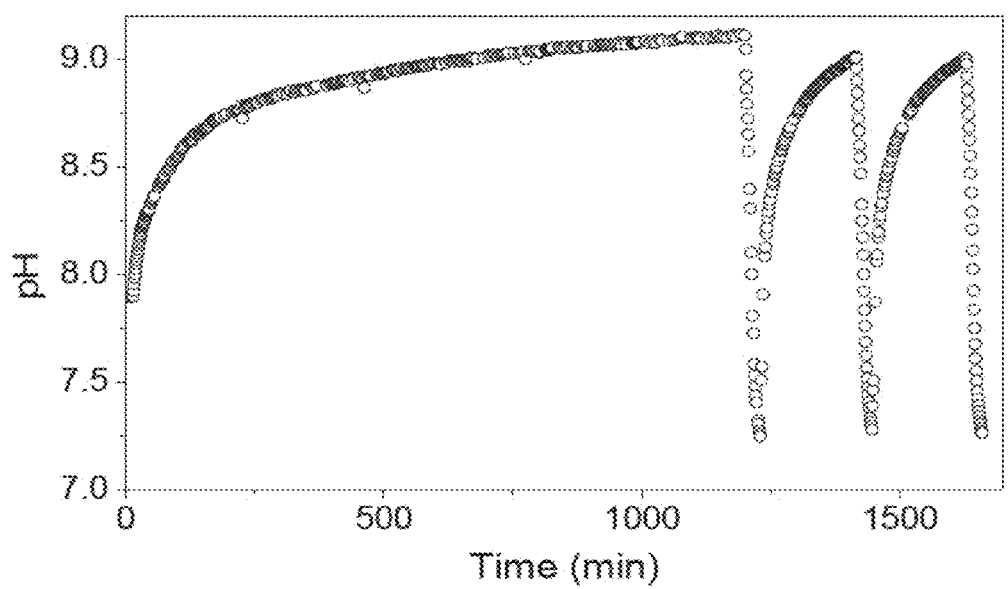
FIG. 20 is a graph depicting fluctuation in pH with sequential regeneration/purification at 35° C.

As shown in FIG. 20, the nutrient recovery process took roughly 20 hours to reach a pH of around 9.2 (~9.6 at adjusted lower temperature). This is lower than the pH achieved in Example 5 due to the higher temperature of the effluent (35° C. compared to 16° C.). Thereafter, the air was shutoff and the biogas was injected into the bubble column, which lasted about 30 minutes before the pH leveled off at around 7.4.

After the pH stabilized, the biogas was shut off and the air was injected into the effluent knocking out $CO_2$ and $H_2S$ that was saturated in the effluent. This regeneration of the effluent raised the pH to around 9.0 and took around 3 hours to complete. This is much faster than the 5 hours it took in Example 5 due to the higher temperature and higher flow rate used in this test. The biogas purification and regeneration process was performed again using the same effluent and similar results were achieved. At the end of the coupled tests, a final purification step was performed to lower the pH of the effluent back to near neutrality so it can be used as a fertilizer.

From the above sequential regeneration/purification design discussed above, tail gas leaving the top of the system was captured and evaluated for determination of the extent to which the biogas can be purified of $CO_2$ through this methodology. FIG. 21 is a summary of that data, with detailed explanation below.

FIG. 21A represents the concentrations of gas components within the biogas that exit the system after gas purification in the approximately pH 9.1 solution. The three runs are not sequential, meaning, the biogas exiting run one was not sent through to run two and so forth. Instead, original raw biogas as defined by the gas cylinder used in the set up was used for each of the three runs.

The results show that by regenerating the anaerobic digester effluent via aeration to increase the pH of the effluent, $CO_2$ (with some residual loss of $CH_4$) can be absorbed into solution and removed from the biogas. Within this study, analysis of the area under the curves using individual and average mass point analysis determines that in each individual step 10-25% of the $CO_2$ content can be removed from the raw biogas. This means that if a sequential approach could be completed, a series of four purification steps (with associated regeneration steps) could conceivably achieve near 0% $CO_2$ content. Importantly, the approximate amount of dissolved methane lost during each individual purification process step was about 1%-2.5%, which when expanded to four sequential operations could result in 4-10% loss of methane to the solution and ultimately the environment.

FIG. 21B depicts gas component analysis of the regeneration step. The data shows that the regeneration step results in immediate loss of some $CH_4$ and a considerable amount of $CO_2$ with continued release, albeit at lower values of $CO_2$ over the course of the three hours.

The data provided herein demonstrates that effluent produced through anaerobic digestion and a nutrient recovery process can be used to remove $H_2S$ from the biogas and can also be used to remove $CO_2$ by regenerating the pretreated effluent for continued use as a physicochemical absorbent. These results show that it is possible to re-aerate the saturated effluent (post biogas purification). Re-aerating the effluent knocked out both $CO_2$ and $H_2S$ from the effluent and because of this raised the pH to >9.

Thereafter, biogas was injected back into the effluent to continue purifying the biogas of $CO_2$. A five step process (biogas purification, regeneration, biogas purification, regeneration, biogas purification) was tested to see if the regeneration process was affected by the multiple steps of purification and regeneration. The results showed that similar pH levels were achieved in each step, which provides evidence that multiple steps could be employed to completely remove both $H_2S$ and $CO_2$ from the biogas to allow biogas from the anaerobic digestion of agricultural manure to be used in more profitable ways than combined heat and power.

Equally important, gas analysis confirmed the knocking out of $CO_2$ during the regeneration step as well as absorption of $CO_2$ during the purification step. Mass analysis (regeneration with purification) can lead to approximately 10-25% reduction in $CO_2$ within the biogas while losing roughly 1-2.5% of the methane. Coupling of four sets of pairs could then conceivably lead to near complete loss of $CO_2$ and purification to useable methane for pipeline or transportation projects.

The invention is now described with reference to the following Examples. These Examples are provided for the purpose of illustration only and the invention should in no way be construed as being limited to these Examples, but rather should be construed to encompass any and all variations that become evident as a result of the teaching provided herein. All references including but not limited to U.S. patents, allowed U.S. patent applications, or published U.S. patent applications are incorporated within this specification by reference in their entirety.

We claim:

1. A method for removing contaminants in a biogas comprising:
    (a) heating and aerating anaerobic digester effluent in an aeration reactor to produce a first effluent with an alkaline pH;
    (b) contacting the first effluent from step (a) with an input biogas in a reactor to produce a treated biogas and a second effluent that has a lower pH as compared to the pH of the first effluent;
    (c) recovering the treated biogas from step (b), wherein the treated biogas has less $H_2S$ as compared to the input biogas;
    (d) aerating the second effluent of step (b) to produce a third effluent, wherein the third effluent has an alkaline pH; and
    (e) contacting the third effluent of step (d) with the recovered biogas of step (c) to remove $CO_2$ in the biogas.

2. The method of claim 1, wherein heating the anaerobic digester effluent comprises using a heat exchanger with the exhaust from a biogas engine as the heated air stream.

3. The method of claim 1, wherein heating the anaerobic digester effluent comprises heating the effluent to a temperature from about 140° F. to about 170° F.

4. The method of claim 1, wherein aerating the anaerobic digester effluent is accomplished using micro-aerators that aerate the effluent at a rate from 5 gallons/cfm to 25 gallons/cfm.

5. The method of claim 1, wherein contacting the alkaline effluent with an input biogas comprises using an alkaline effluent with a pH from about 9.0 to about 12.0.

6. The method of claim 1, wherein contacting an input biogas with the alkaline effluent comprises using a bubble column reactor.

7. The method of claim 6, wherein the bubble column reactor has an inlet orifice sparger.

8. The method of claim 6, wherein the bubble column has a churn-turbulent flow regime.

9. The method of claim 1, wherein contacting the alkaline effluent with an input biogas comprises a gas:liquid ratio selected from the group consisting of: 20:1, 21:1, 22:1, 23:1, 24:1, 25:1, 26:1, 27:1, 28:1, 29:1, and 30:1.

10. The method of claim 1, wherein contacting the alkaline effluent with an input biogas comprises a gas:liquid ratio of 21-25:1.

11. A method for removing contaminants in a biogas comprising:
    (a) aerating an anaerobic digester effluent that has previously been mixed with a biogas; and (b) remixing the aerated anaerobic digester effluent of step (a) with the same biogas that had previously been mixed with an anaerobic digester effluent to remove contaminants from the biogas.

* * * * *